United States Patent [19]

Berry et al.

[11] Patent Number: 5,158,534
[45] Date of Patent: Oct. 27, 1992

[54] AUTOMATED GAS DELIVERY SYSTEM FOR BLOOD GAS EXCHANGE DEVICES

[75] Inventors: Gaylord L. Berry, Salt Lake City, Utah; Yansong Shan, Ann Arbor, Mich.

[73] Assignee: CardioPulmonics, Inc., Salt Lake City, Utah

[21] Appl. No.: 548,290

[22] Filed: Jul. 3, 1990

[51] Int. Cl.$^5$ .............................................. A61M 2/14
[52] U.S. Cl. .......................................... 604/4; 604/6; 422/44
[58] Field of Search .................. 604/4, 5, 26, 30; 128/DIG. 3; 422/44, 45, 48

[56] References Cited

U.S. PATENT DOCUMENTS

| | | | |
|---|---|---|---|
| 3,533,408 | 10/1970 | Paoli | 128/214 |
| 3,927,980 | 12/1975 | Leonard | 23/258.5 |
| 3,946,731 | 3/1976 | Lichtenstein | 128/214 |
| 4,207,887 | 6/1980 | Hildebrandt et al. | 604/4 |
| 4,231,366 | 11/1980 | Schael | 128/214 |
| 4,401,431 | 8/1983 | Arp | 604/4 |
| 4,464,932 | 8/1984 | Ewing et al. | 73/204 |
| 4,464,932 | 8/1984 | Ewing et al. | 73/204 |
| 4,466,804 | 8/1984 | Hino | 604/4 |
| 4,490,331 | 12/1984 | Steg, Jr. | 422/46 |
| 4,493,692 | 1/1985 | Reed et al. | 604/4 |
| 4,583,969 | 4/1986 | Mortensen | 604/49 |
| 4,638,811 | 1/1987 | Bisera et al. | 128/673 |
| 4,650,457 | 3/1987 | Morioka et al. | 604/4 |
| 4,661,092 | 4/1987 | Popovich et al. | 604/26 |
| 4,828,543 | 5/1989 | Weiss et al. | 604/4 |
| 4,850,958 | 7/1989 | Berry et al. | 604/26 |

Primary Examiner—Robert A. Hafer
Assistant Examiner—Kerry Owens
Attorney, Agent, or Firm—Workman, Nydegger & Jensen

[57] ABSTRACT

A system for delivering oxygen to a gas permeable membrane oxygenator is disclosed. The system may include an integral source of gas under pressure and a source of vacuum. A first mass flow controller is connected to the source of gas upstream in the gas flow from the gas exchange device. A pressure valve is positioned in the gas flow between the first mass flow controller and the membrane oxygenator. An atmospheric vent is positioned between the pressure valve and the first mass flow controller. A second mass flow controller is positioned downstream from the gas exchange device and is connected to the source of vacuum. A central controller commands the pressure valve to maintain the pressure at the inlet of the gas exchange device at a subatmospheric pressure. The second mass flow controller is commanded to maintain a rate of flow which is desired through the gas exchange device. The first mass flow controller is commanded to maintain a rate of flow higher than the second mass flow controller to ensure that a sufficient flow of gas is available through the pressure valve and the gas exchange device. The excess gas is exhausted through the vent. The present invention ensures sufficient gas flow at the gas permeable membrane to provide transfer of gases with the blood. Also, the pressure of the gas within the membrane oxygenator is low enough that outgassing through the membrane of bubbles into the blood is avoided.

29 Claims, 10 Drawing Sheets

AUTOMATED GAS DELIVERY SYSTEM FOR BLOOD GAS EXCHANGE DEVICES

A portion of the disclosure of this patent document contains material to which a claim of copyright protection is made. The copyright owner has no objection to the facsimile reproduction by any one of the patent document or the patent disclosure as it appears in the Patent and Trademark Office patent file or records, but reserves all other rights in the copyrighted work.

BACKGROUND

1. The Field of the Invention.

The present invention relates to methods and apparatus for performing extrapulmonary blood gas exchange wherein blood receives oxygen and releases carbon dioxide. More particularly, the present invention relates to systems used to deliver ventilatory gases to extrapulmonary blood gas exchange devices.

2. The Prior Art

Thousands of patients in hospitals suffer from inadequate blood gas exchange, which includes both inadequate blood oxygenation and inadequate removal of carbon dioxide ($CO_2$). These conditions are commonly caused by varying degrees of respiratory inadequacy usually associated with acute lung illnesses such as pneumonitis, atelectasis, fluid in the lung, or obstruction of pulmonary ventilation. Various heart and circulatory aliments such as heart disease and shock can adversely affect the flow of blood and thereby also reduce the rate of blood gas exchange.

Currently the most widely used methods of treating these types of blood gas exchange inadequacies involve increasing the flow of oxygen through the lungs by either increasing the oxygen concentration of the inspired gases or by mechanically ventilating the lungs. Both methods result in placing further strain on the lungs, which may be diseased and unable to function at full capacity. In order to allow diseased or injured organs to heal it is generally best to allow these organs a period of rest followed by a gradual increase in activity.

Various devices have been developed which are capable, at least for a limited period of time, of taking over the gas exchange function of the lungs. Many blood oxygenators are in common use and are employed most frequently during heart surgery. Such commonly available devices are capable of providing blood oxygenation and carbon dioxide removal sufficient to carry the patient through the surgical procedure but are not intended to provide pulmonary support for more than the hours required to perform the surgery. These oxygenators include devices which bubble oxygen into the blood as the blood flows through the device. This is usually followed by a portion of the device which removes the bubbles in the blood to make it acceptable for reintroduction into the patient.

Another group of blood oxygenators employ gas permeable membranes. These devices take many different shapes and configurations; however, the basic concept of operation is the same in all of these devices. Blood flows on one side of the gas permeable membranes while a ventilatory gas, i.e., oxygen, flows on the other side of the membrane. As the blood flows through the device the oxygen diffuses, on a molecular level, across the gas permeable membrane and enters the blood. Likewise, carbon dioxide present in the blood diffuses across the gas permeable membrane and enters the gas phase.

Of the available blood oxygenators, those incorporating gas permeable membranes may be best used in long term applications (e.g., one to seven days) as a pulmonary assist device for a patient suffering from acute respiratory failure. In the case of cardiopulmonary bypass where all of the patient's gas exchange needs must be supplied by the oxygenator, constant attention by a trained perfusionist is necessary to guard the welfare of the patient.

The use of a blood oxygenator as a pulmonary assist device also requires constant vigilance if maximum blood gas transfer is to take place. As will be appreciated, the condition of the patient may change from hour to hour, or minute to minute. Such changes often require a change in the operation of a blood oxygenator in order to maintain efficient blood gas transfer. Significantly, some changes in a patient's condition can lead to serious consequences if corresponding changes are not made in the oxygenator's operation. For example, "outgassing," or the forcing of undissolved gas through the membrane into the blood as bubbles where they can form gas emboli, may occur if the blood phase pressure drops dramatically and the gas phase pressure at the permeable membrane is allowed to remain above the blood phase pressure.

In general, perfusionists are able to satisfactorily control the operational characteristics of blood oxygenators using manual control techniques over the duration of a surgical procedure lasting many hours with an acceptably low incidence of operator and equipment related accidents. It will, however, be appreciated that as the length of time a patient is undergoing pulmonary support increases to several days, the likelihood of operator error greatly increases. Furthermore, many of the parameters which must be considered in order to maximize patient welfare are not easily ascertainable using manual techniques. All of these considerations must be addressed when planning to use a pulmonary assist device on a long term basis.

In view of the foregoing, it would be an advance in the art to provide a blood oxygenator gas delivery system which is safer to use than previous available ventilatory gas delivery systems and which can be used with a membrane oxygenator to more efficiently transfer oxygen to, and carbon dioxide from, the blood. It would also be an advance in the art to provide a blood oxygenator gas delivery system wherein the gas phase is always maintained at a low enough pressure to ensure that formation of gas emboli in the blood does not occur and wherein the flow of the gas is precisely and automatically controlled. It would be yet another advance in the art to provide a blood oxygenator gas delivery system which may be easily set up and operated for long periods of time without constant attention from a technician.

OBJECTS AND BRIEF SUMMARY OF THE INVENTION

In view of the above described state of the art, the present invention seeks to realize the following objects and advantages One primary object of the present invention is to provide a blood oxygenator gas delivery system which is safer to use than previous available manual or automatic ventilatory gas delivery systems.

It is another object of the present invention to provide a blood oxygenator gas delivery system which maintains more efficient oxygen and carbon dioxide transfer with the blood than previously known devices.

It is also an object of the present invention to provide a blood oxygenator gas delivery system wherein the gas phase is always maintained at a pressure below the blood phase pressure to ensure that formation of gas emboli in the blood does not occur.

It is a further object of the present invention to provide a blood oxygenator gas delivery system wherein the flow of the gas is precisely and automatically controlled.

It is another object of the present invention to provide a blood oxygenator gas delivery system which may be easily set up and operated for long periods of time without constant attention from a technician.

These and other objects and advantages of the invention will become more fully apparent from the description and claims which follow, or may be learned by the practice of the invention.

Briefly summarized, the foregoing objects are achieved by a system for controlled delivery of ventilatory gases which includes means for adjusting the pressure of a ventilatory gas which is delivered to the gas permeable membrane of a blood gas exchange device, such as an extracorporeal or intracorporeal blood gas exchange device. The means for adjusting the pressure of the gas ensures that the pressure of the ventilatory gas present at the gas permeable membrane is maintained at a pressure which is at least below the central venous pressure of the patient in the case of an intracorporeal gas exchange device and at least below the ambient atmospheric pressure in the case of an extracorporeal gas exchange device. Preferably, the gas phase pressure at the gas permeable membrane is maintained below the ambient atmospheric pressure at all times. By keeping the pressure of the gas phase at the gas permeable membrane to such a low value, outgassing and formation of gas emboli in the patient's blood is avoided.

Also included in the present invention is a means for regulating the mass of the gas flowing to the gas permeable membrane to ensure that sufficient gas flows through the pulmonary assist device to maintain proper gas transfer. Importantly, in order to support a patient's metabolism a minimum amount of carbon dioxide must pass out of the patient's blood and oxygen must pass into the red blood cells. The means for regulating the mass of the gas flowing to the gas permeable membrane ensures that the gas flow is sufficient to ensure a minimum amount to oxygen is present at the gas permeable membrane and that the gas flow is sufficient to remove the carbon dioxide which passes out of the blood.

By including a means for adjusting the pressure of the gas at the gas permeable membrane, safety is assured. By adjusting the gas phase pressure at the gas permeable membrane to a value which is at least less than the patient's central venous pressure in the case of an intracorporeal gas exchange device, or preferably less than the ambient atmospheric pressure in the case of all gas exchange devices, outgassing of oxygen into the blood and the formation of gas emboli is avoided. The formation of gas emboli is potentially life threatening.

While the means for adjusting the pressure of the gas safely provides that outgassing and air emboli are avoided, the means for regulating the mass of the gas flowing to the gas permeable membrane safely ensures that sufficient oxygen and carbon dioxide transfer will occur across the gas permeable membrane. Thus, gas exchange is carried out with the greatest safety and effectiveness.

DETAILED DESCRIPTION OF THE PREFERRED EMBODIMENTS

Figure 1:
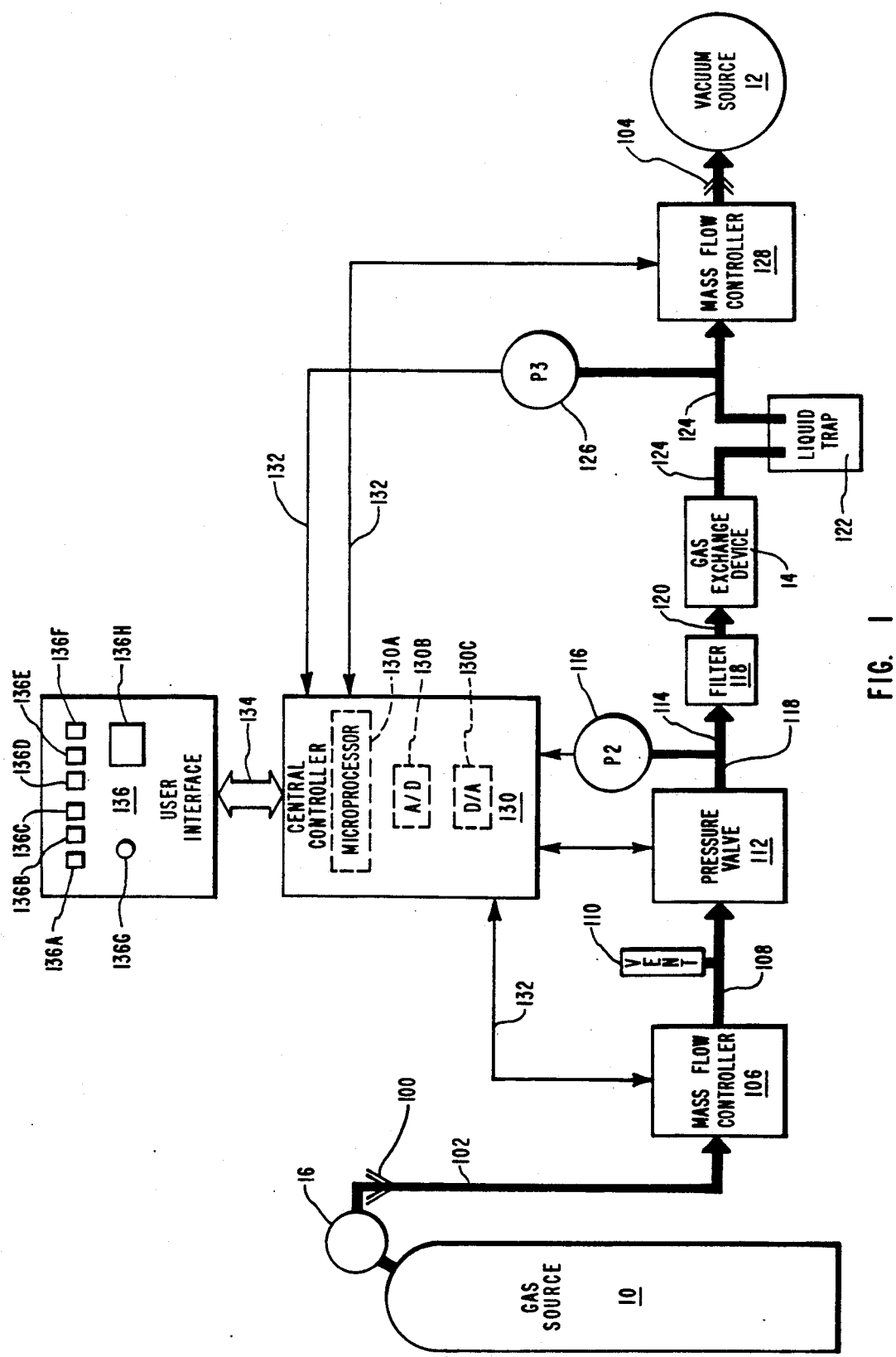
FIG. 1 is a block diagram of a presently preferred embodiment of the gas delivery system for blood oxygenators of the present invention.

Reference will now be made to the drawings wherein like structures will be provided with like reference designations.

Proper oxygenation of a patient's blood is critical to the survival of a patient. In accordance with the current state of the art, during a surgical procedure involving pulmonary bypass, a highly trained perfusionist attends to the oxygenation devices. The duties of the perfusionist includes making sure that sufficient blood gas transfer takes place and that bubbles formed in the blood do not enter the patient's circulatory system where they might form gas emboli in vital organs causing blockage of blood flow to critical areas.

Due to the attentive care provided by perfusionists, the number of injuries and fatalities occurring due to perfusion errors during cardiopulmonary bypass is very low. Nevertheless, the human errors of a perfusionist do result in fatal mistakes during cardiopulmonary bypass procedures. Surgical procedures involving cardiopulmonary bypass may last many hours.

In contrast to the duration of many surgical procedures involving cardiopulmonary bypass, the use of pulmonary assist devices during acute respiratory failure is necessary for long periods of time (e.g., days or weeks rather than hours). The longer duration of providing pulmonary assist during acute respiratory failure makes the likelihood of human error much more significant.

Moreover, when using intracorporeal gas exchange devices such as those described in U.S. Pat. Nos. 4,583,969 and 4,850,958 it is more difficult to accurately control the flow of gas, and control the pressure of the gas, where the gas permeable membrane is wholly hidden in the patient's body. U.S. Pat. Nos. 4,583,969 and 4,850,958 are incorporated herein by reference.

A further concern which is encountered when dealing with intracorporeal, e.g., intravenous, gas exchange devices is that conditions within the body may change relatively quickly. The changes which occur within a patient's body may go unnoticed using prior art techniques and appropriate corrections can go unmade. The fact that the gas permeable membrane is within the patient's body requires that corrections be made synchronously with changing conditions to avoid the occurrence of outgassing. When using intravenous gas exchange devices, any gas bubbles which do form due to outgassing will immediately travel to the patient's blood stream without any opportunity to be noticed and eliminated.

As will be better appreciated after examination of this disclosure, the embodiments and methods of the present invention provide the greatest possible safety for a patient during complete cardiopulmonary bypass or whose life functions are being supported by a pulmonary assist device. First, the present invention assures that the gas phase pressure present at the gas permeable membrane of the membrane oxygenator is low enough that outgassing does not occur. Second, the present invention assures that sufficient gas flows past the gas permeable membrane so that adequate oxygen and carbon dioxide transfer takes place.

Referring now to FIG. 1, a block diagram of the presently preferred embodiment of the present invention is provided.

As represented in FIG. 1, the embodiments of the present invention are intended to be used with a membrane gas exchange device, represented at 14 and having an inlet and an outlet, which may be either an extracorporeal device or an intracorporeal (intravenous or intra-arterial) device. As explained, the need for the present invention is greatest when a gas exchange device is implanted into a patient where outgassing may have disastrous results and the relatively long term use of the device makes constant attention by an attendant unsuitable. Also represented in FIG. 1 is a gas source 10 and a vacuum source 12. The gas source 10 may be a commonly available source of ventilatory gas, i.e., oxygen, such as a pressurized tank, which can be incorporated into the embodiment of the present invention or independent thereof. Alternatively, the gas source 10 may be the oxygen distribution system of a medical facility such as a hospital.

Also represented in FIG. 1 is a tank pressure regulator 16 which is commonly known in the art. Those skilled in the art will understand the advantages of regulating the gas source 10 to stabilize the pressure which is supplied and also how to carry out the regulation.

The vacuum source 12 represented in FIG. 1 may be an independent source of vacuum such as that supplied by the vacuum distribution system of a medical facility or, preferably, a dedicated source of vacuum which is incorporated into the embodiment of the present invention. In the case of a dedicated vacuum source, it is preferred that one commercially available from KNF Neuberger, Inc. model no. PV392-726-12.89 be used. It will also be appreciated that regulation of the source of vacuum, to some extent, may be desirable so that the pressure exerted is relatively constant.

As shown in FIG. 1, a gas flow or gas stream is established from the gas source 10 through an gas exchange device 14 to the vacuum source 12 In FIG. 1, the gas flow path is indicated by heavier lines (102, 108, 114, 120, and 124) with arrows showing the direction of the flow and lighter lines (132) being used to represent electrical control/data signal paths. For example, it is preferred that the heavier lines represent ⅛ inch inner diameter tubing which is suitable for use in medical applications.

The structures of the preferred embodiment described herein are intended to ensure the greatest possible safety to the patient both by providing adequate gas flow at the gas permeable membrane and by preventing any incidents of outgassing.

Shown in FIG. 1 is a connector 100 which functions as a means for receiving a gas under pressure from a gas source. In the illustrated embodiment, the gas source is an external tank of oxygen. Other supplies of ventilatory gases as described above and as known in the art can also serve as a gas source and the means for receiving a gas under pressure is intended to include any structure performing an equivalent function to that performed by the connector 100. Also represented in FIG. 1 is another connector 104 which is the presently preferred example of the means for connecting to a source of vacuum.

Represented in FIG. 1 are two pressure sensors 116 (P2) and 126 (P3). Each of the pressure sensors 116 and 126 are preferably those which are commercially available from Sensyn with pressure sensor 116 preferably being model no. 142SC01D and pressure sensor 126 being model no. 142SC05D. Another pressure sensor (referred to as P1 in the programming code appended hereto) which is not represented in FIG. 1 can be positioned to sense the pressure of the gas in line 102.

It will be appreciated that the pressure sensed by the pressure sensor 126 will be less than the pressure sensed by the pressure sensor 116, depending on the mass flow rate of the ventillatory gas. Thus, a significant pressure drop occurs across the gas exchange device 14. Each of the pressure sensors 116 and 126 outputs an electrical signal output corresponding to the pressure which is sensed.

As shown in FIG. 1, two mass flow controllers 106 and 128 are positioned in the gas flow. The mass flow controllers are preferably those which are commercially available from MKS Instruments, Inc. of Andover, Mass. utilizing apparatus and methods described in U.S. Pat. No. 4,464,932 which is incorporated herein by reference. It is preferred that mass flow controller 106 be model no. 1159B-05000RB-SP sensing a flow range of from 0 to 5000 standard cubic centimeters per minute (sccm). It is also preferred that mass flow controller 128 be model no. 1159B-05000B-SP sensing a flow range of from 0 to 3000 sccm. The preferred mass flow controllers are capable of sensing and controlling the mass of the gas flowing therethrough with a high degree of precision.

Each of the described mass flow controllers are an example of a flow control means or a means for regulating the mass of the gas flowing to the gas permeable membrane. As taught herein, the present invention may be carried out in other forms including only one mass flow controller or an equivalent functioning device. Thus, any structure performing functions which are equivalent to those carried out by one of the mass flow controllers described herein is intended to fall within the scope of the means for regulating the mass of the gas flowing to the gas permeable membrane of the gas exchange device.

Also represented in FIG. 1 is a pressure valve 112 and a vent 110. The function of pressure valve 112 and vent 110 is to adjust the pressure of the gas present within the gas exchange device. Since the avoidance of outgassing is of crucial importance in the embodiments of the present invention, the pressure of the gas within the gas exchange device must be kept at least as low as the patient's central venous pressure in the case of an intracorporeal gas transfer device and, as is done in the case of the described embodiment, preferably at least as low as the ambient atmospheric pressure.

The pressure valve 112 is preferably one also available from MKS Instruments, Inc. as model no. 0248A-50000RV. The pressure valve 112 is adapted to receive an electrical signal command and adjusts its output pressure accordingly.

With pressure valve 112 commanded to maintain a subatmospheric pressure, preferably −15 mm Hg, the vacuum exerted by the vacuum source 12 downstream from the pressure valve 112 causes gas to be drawn through the pressure valve 112. In order to ensure enough flow through the gas exchange device 14, the flow rate through mass flow controller 106 is set higher than the flow rate through mass flow controller 128. In the described embodiment, it is preferred that the flow through mass flow controller 106 is set at about 20 per cent higher than the flow through mass flow controller 128.

In order to prevent a build up of pressure on the upstream side of the pressure valve 112, the vent 110 is provided. The vent 110 has a cross sectional area which is sufficient to allow the necessary amount of gas to escape without undue resistance. During normal operation, gas is continually exhausted to some extent through the vent 110. Thus, the entry of contaminants through the vent 110 against the flow of the gas is not a significant concern.

The pressure valve 112 is one presently preferred example of a pressure control means or a means for adjusting the pressure of the gas received from the gas source 10 so as to prevent outgassing. As will be explained shortly and as appreciated by those skilled in the art, other arrangements and devices can perform functions equivalent to those performed by the described pressure valve. It is intended that such other arrangements and devices be included within the scope of the means for adjusting the pressure of the gas included in the present invention.

Still referring to FIG. 1, a bacteriological filter 118, such as is commercially available in the art, is present in the gas flow immediately before the gas exchange device 14. A liquid trap 12 is also present in the gas flow immediately after the gas exchange device 14. The liquid trap 120 is used to remove any liquid which has appeared in the gas flow after passing through the gas exchange device and which might otherwise interfere with the operation of the mass flow controller 128.

Also represented in FIG. 1 is a central controller 130. The components which generate, or respond to, electrical control signals are connected to the central controller 130 by various control lines as represented at 132. The central controller 130 preferably includes a microprocessor 130A, an analog to digital converter 130B, and a digital to analog converter 130C, if necessary, to communicate with the other components. The central controller 130 is the presently preferred example of a control means of the present invention.

A user interface, 136 in FIG. 1, may comprise visual and/or audio signals and displays to indicate to medical personnel the operational status of the system. For example, in the described embodiment, six LEDs 136A-136F, or abnormal operating indicators, are provided to indicate to medical personnel that portions of the system are operating in a normal state or that a problem is present. Also represented in connection with the user interface 130 is a digital display H, or a flow rate display, and a user operable control 135G with which the user can select the flow rate through the gas exchange device. The user interface 136 communicates with the central controller 130 by way of a bus represented at 134.

A detailed schematic diagram of the presently preferred configuration for the central controller 130 is provided in FIGS. 4A-4F. The programming code for the microprocessor included in the central controller 130 is provided in the programming code appendix attached hereto.

After examining the structure of the described embodiment, those skilled in the art will appreciate that other equivalent arrangements may be used to accomplish the objectives of the present invention. For example, a single mass flow controller (functioning as a means for regulating the mass of the gas stream) could be located upstream from the gas exchange device, a pressure sensor positioned immediately at the inlet to the gas exchange device, and a pressure valve (functioning as a means for regulating the pressure) located downstream from the gas exchange device.

In another example of a potential embodiment within the scope of the present invention, a single mass flow controller could be positioned in the flow stream downstream from the gas exchange device with a vent and pressure valve positioned upstream from the gas exchange device as represented in FIG. 1. Furthermore, a single mass flow controller could be positioned downstream from the gas exchange device and a variable vacuum pump utilized to vary the pressure exerted thereon. While such arrangements are possible, they are not presently preferred because of the present potentially unstable operation using presently available components. Since it is an objective to provide the safest possible implementation of the present invention, the described embodiment is preferred. It is within the scope of the present invention, however, to utilize other arrangements of the described structures to accomplish the same or equivalent functions.

The operation of the structures represented in FIG. 1 is controlled principally by microprocessor 130A and the presently preferred programming code for the microprocessor is attached hereto. It is to be appreciated that devices other than the described microprocessor and its associated devices can function as the control means of the present invention.

Reference will now be made to the flow chart of FIGS. 2A-2B and to the block diagram of FIG. 1 to describe the presently preferred method of the present invention. Beginning at Start 200 in FIG. 2A, the flow through the gas exchange device is set to zero as represented at step 202. A zero flow control command is read at step 204 by the controller 130 and the apparatus waits until the flow sensed by the mass flow controller is actually zero.

Figure 2A:
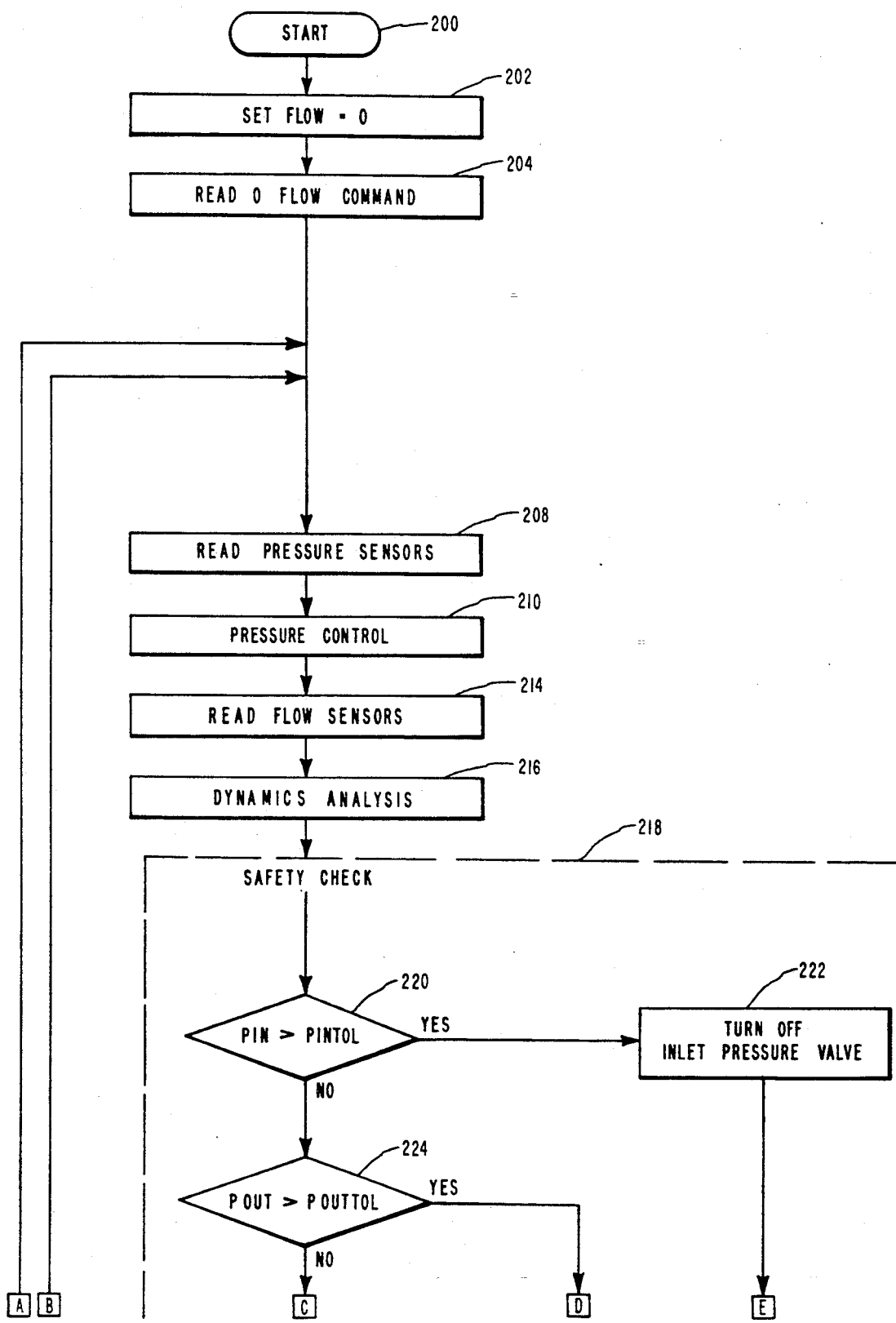
FIGS. 2A-2B are a flow chart showing the steps carried out by the system represented in FIG. 1.
Figure 2B:
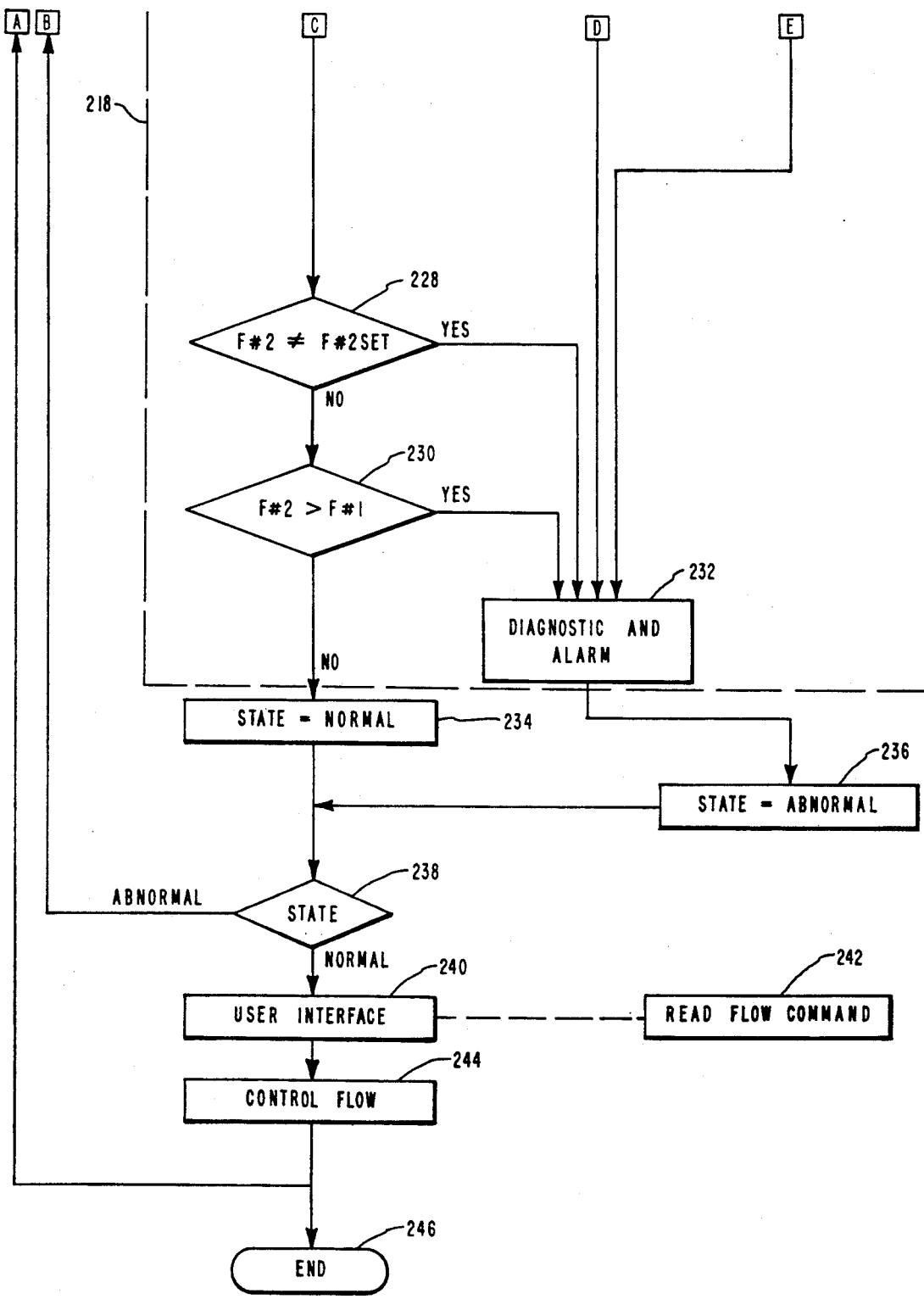

Referring still to FIG. 2A, in the next step 208 the pressure sensors 116 and 126 are read. As explained, it is crucial to maintain the gas phase pressure within the gas exchange device 14 at a value which is at least less than the lowest blood pressure of the patient, in the case of an intracorporeal gas exchange device, and preferably less than the ambient atmospheric pressure in all cases. This is accomplished in the described embodiment by maintaining the pressure in the gas exchange device at a subatmospheric value. Reading pressure sensors 116 and 126 provides a check that the pressure at the gas permeable membrane is within acceptable values. If necessary, the pressure may be regulated by altering the command presented to the pressure valve 112 by the central controller 130 as indicated at step 210.

The flow sensors which are integral with the mass flow controllers 106 and 128 are read as shown at step 214 and a dynamics analysis step 216 takes place wherein the described embodiment analyzes the characteristics of the flow of gas through the particular gas exchange device in conjunction with a particular patient and gas exchange device. As an example of a useful type of dynamic analysis which may be carried out is to determine the resistance of the gas exchange device to the flow of gas therethrough by examining the pressure drop across the gas exchange device and the flow therethrough. Other types of dynamic analysis may also be beneficially carried out.

Performed next is a series of steps which are included within the dashed box labeled safety check 218. The steps of included within the safety check 218 are intended to find and identify the source of an "out-of-tolerance" value so that corrective action can be taken.

At step 220, the pressure at the inlet of the gas exchange device (PIN), sensed by pressure sensor 116, is compared to a tolerance value (PINTOL), and if the tolerance value is exceeded, then a decision is made at step 220 to turn off the pressure valve 112 by the central controller 130 (step 222) and enter into a diagnostic and alarm routine as indicated at step 232. The tolerance pressure for the inlet of the gas exchange device (PINTOL) may be 0 mm Hg, for example, if the target pressure for the pressure valve 112 is set at −15 mm Hg.

If the pressure at the inlet of the gas exchange device (PIN) is less than the expected value (PINTOL) at step 220, then the process proceeds to step 224 where it is determined whether the pressure at the outlet of the gas exchange device (POUT) is greater than the tolerance value (POUTTOL) as sensed by the pressure sensor 126. If the pressure at the outlet of the gas exchange device is greater than the tolerance value, then the diagnostic and alarm routine 232 is entered. If the pressure at the outlet of the gas exchange device is less than or equal to the proper value, the process moves on to step 228.

Similarly, to the previous steps, in step 228, if the gas flow through mass flow controller 128 (F#2) is greater than or less than (i.e., unequal) to the flow command presented to the mass flow controller 128 (F#2SET), then the diagnostic and alarm routine 232 is invoked. In the operation of the described embodiment, it is the flow through mass flow controller 128 which is of crucial importance since that gas flow is also the precise flow through the gas exchange device. Also, in step 230, if the gas flow through mass flow controller 128 is greater than the gas flow through mass flow controller 106, then the diagnostic and alarm routine 232 is called.

If the decisions made at steps 220, 224, 228, and 230 are all "no," the state of the system is normal as indicated at step 234. If after calling the diagnostic and alarm routine 232 an abnormality is detected in the system (as represented at 236), the decision at step 238 is made to rerun the loop which comprises the steps of the safety check 218 to continue to alert the user of the abnormality which has been detected.

If the state of the system is normal, the user interface 136 is checked for the flow command which may have been input (step 240) and the flow command entered thereat is read (step 242). The flow command is entered into the central controller 130 of the described embodiment and is determined by a medical professional in accordance with the needs of the patient and considering the particular gas exchange device being used. When the operational parameters are altered, care must be taken to avoid exceeding the pressure which can be tolerated in the gas exchange device. Occurrences such as "overshoot" which might occur when the pressure valve 112 or the mass flow controllers 106 and 128 are presented with an altered command. Moreover, the embodiment should be designed such that electrical and physical noise does not cause the significant problems.

When using the described embodiment, the flow command causes the mass flow controller 128 to be set to the flow rate which will result in that rate of flow through the gas exchange device. The mass flow controller 106, which is positioned upstream from the gas exchange device 14, is set to maintain a flow at specific amount, preferably 20 per cent above that maintained by mass flow controller 128. Once the flow command is read (step 242) the flow is controlled by the system and a loop beginning at step 208 is entered and repeated. The gas flow continues to be controlled (step 244) until the system is shut down as represented at the End step 246 shown in the flow chart.

It will be appreciated that with mass flow controllers 106 and 128 commanded as described, there will be a continual flow of gas out of the vent 110 and the flow set by the mass flow controller 128 will be the actual gas flow at the gas permeable membrane through the gas exchange device. Once the flow command has been read and implemented, the described embodiment will provide that the sufficient flow through the gas exchange device 14 occurs without interruption.

Figure 3:
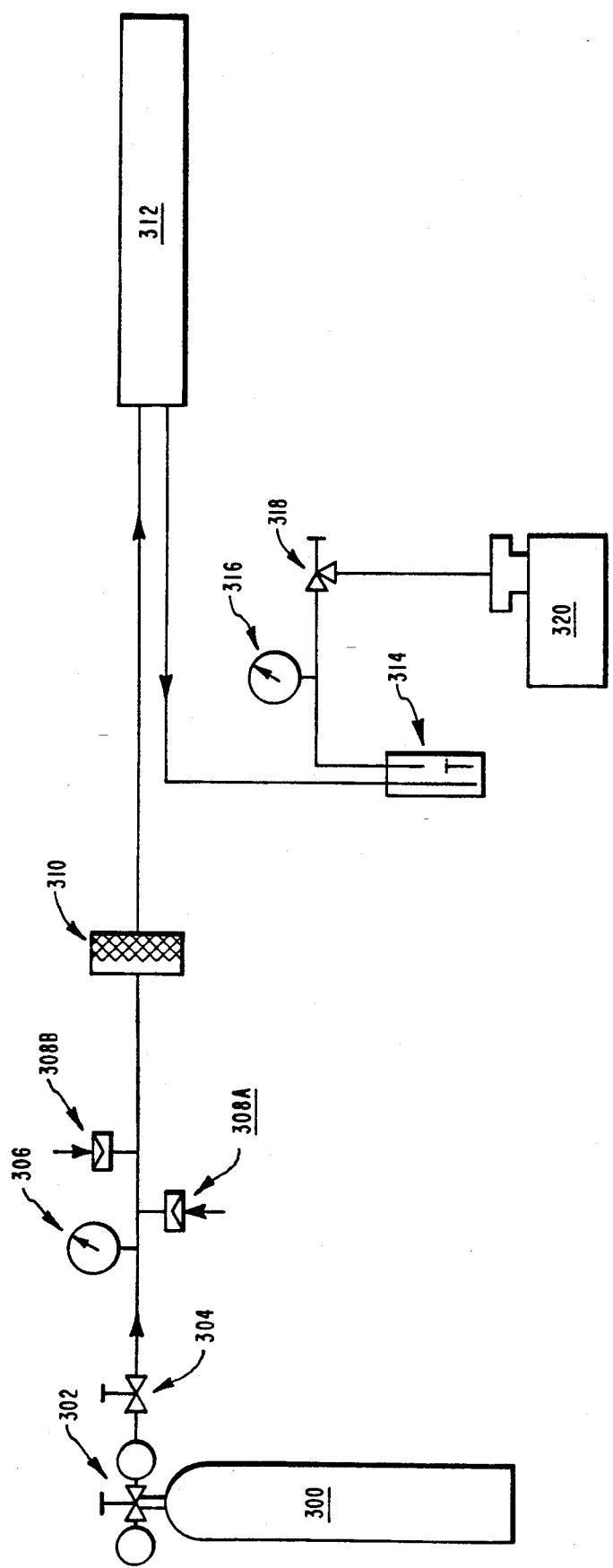
FIG. 3 is a diagram showing another apparatus which may be used to carry out the method of the present invention.
Figure 4A:
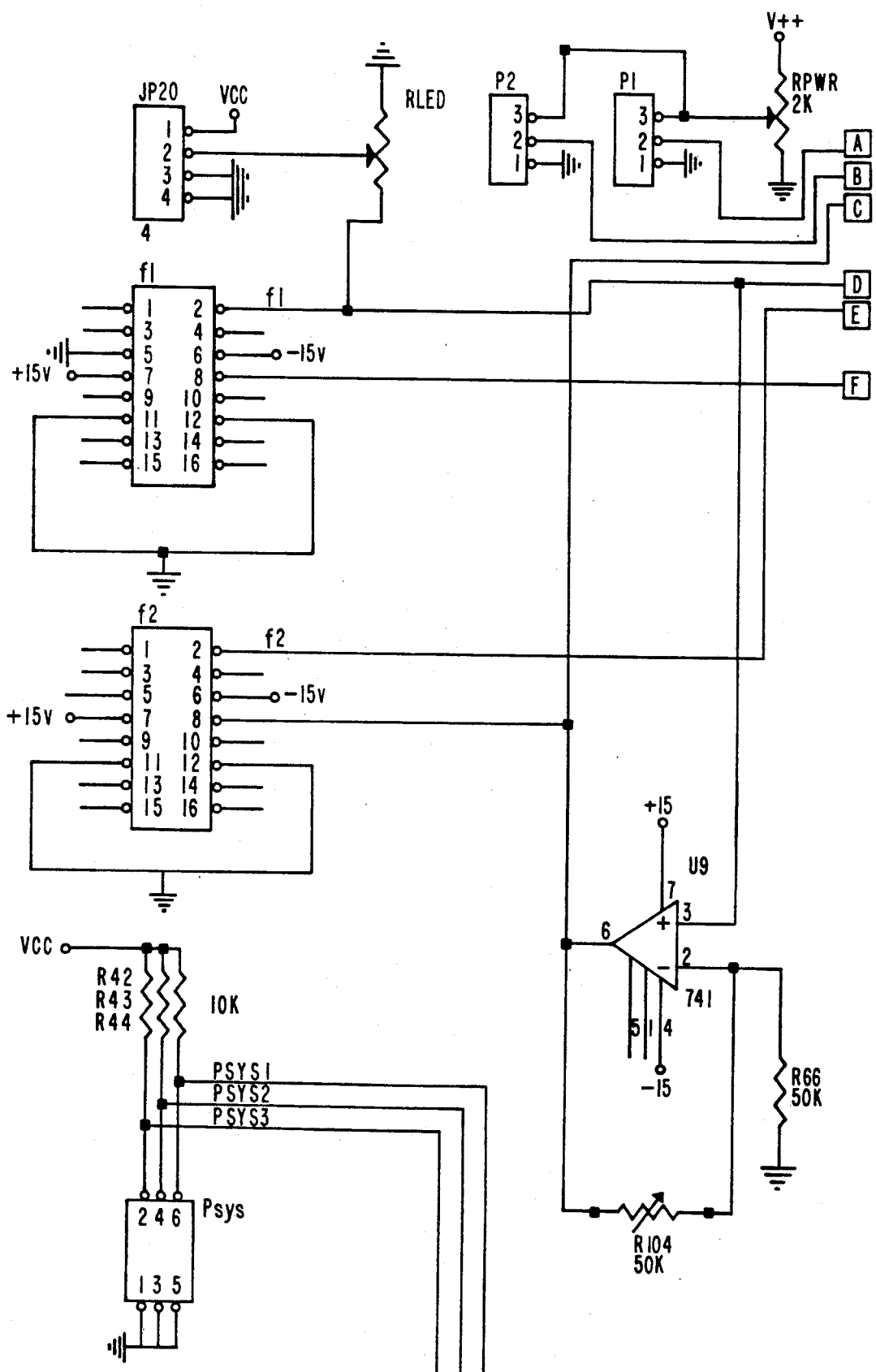
FIGS. 4A-4F are a detailed schematic circuit diagram of presently preferred implementation of central controller portion of the system represented in FIG. 1.
Figure 4B:
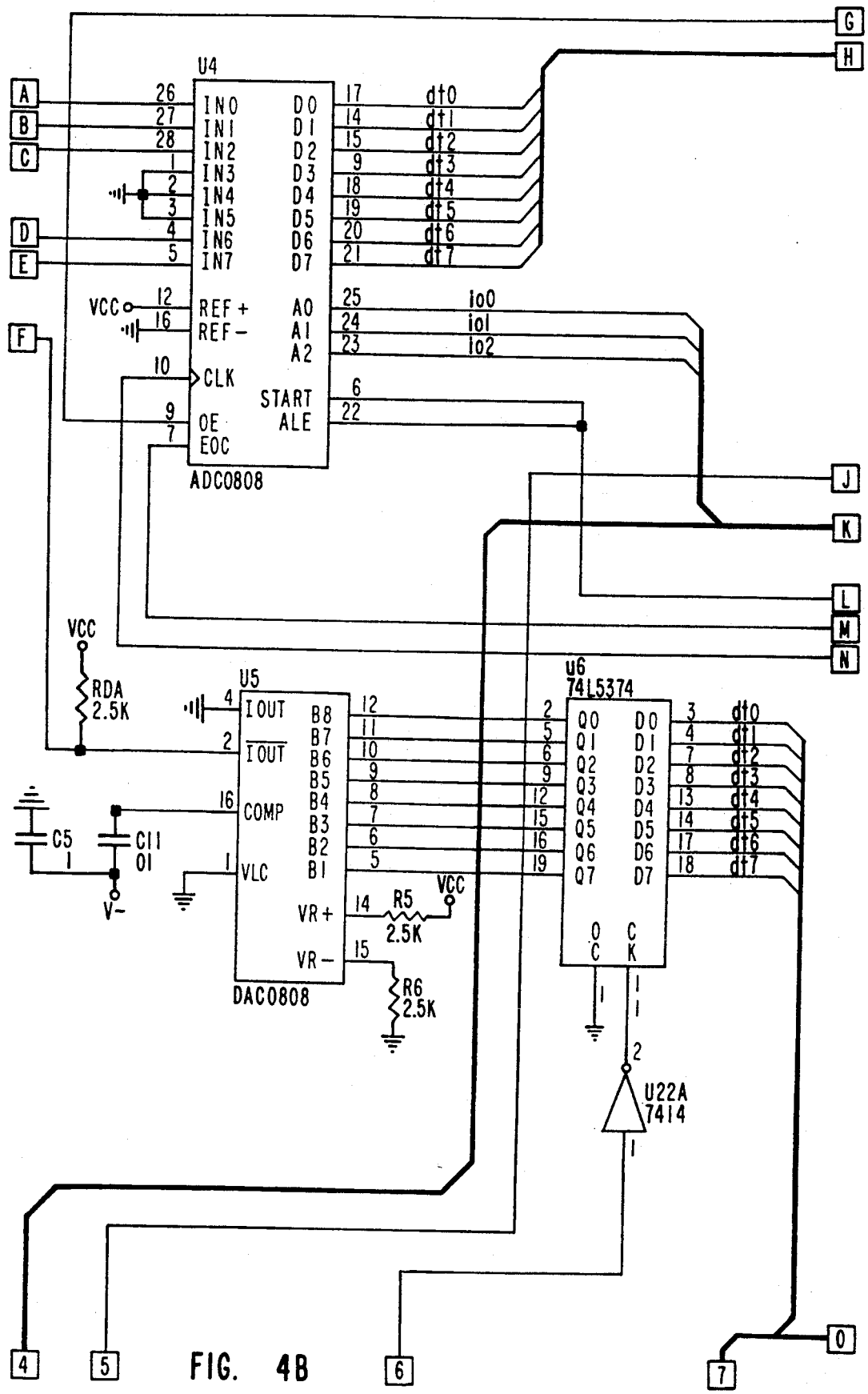
Figure 4C:
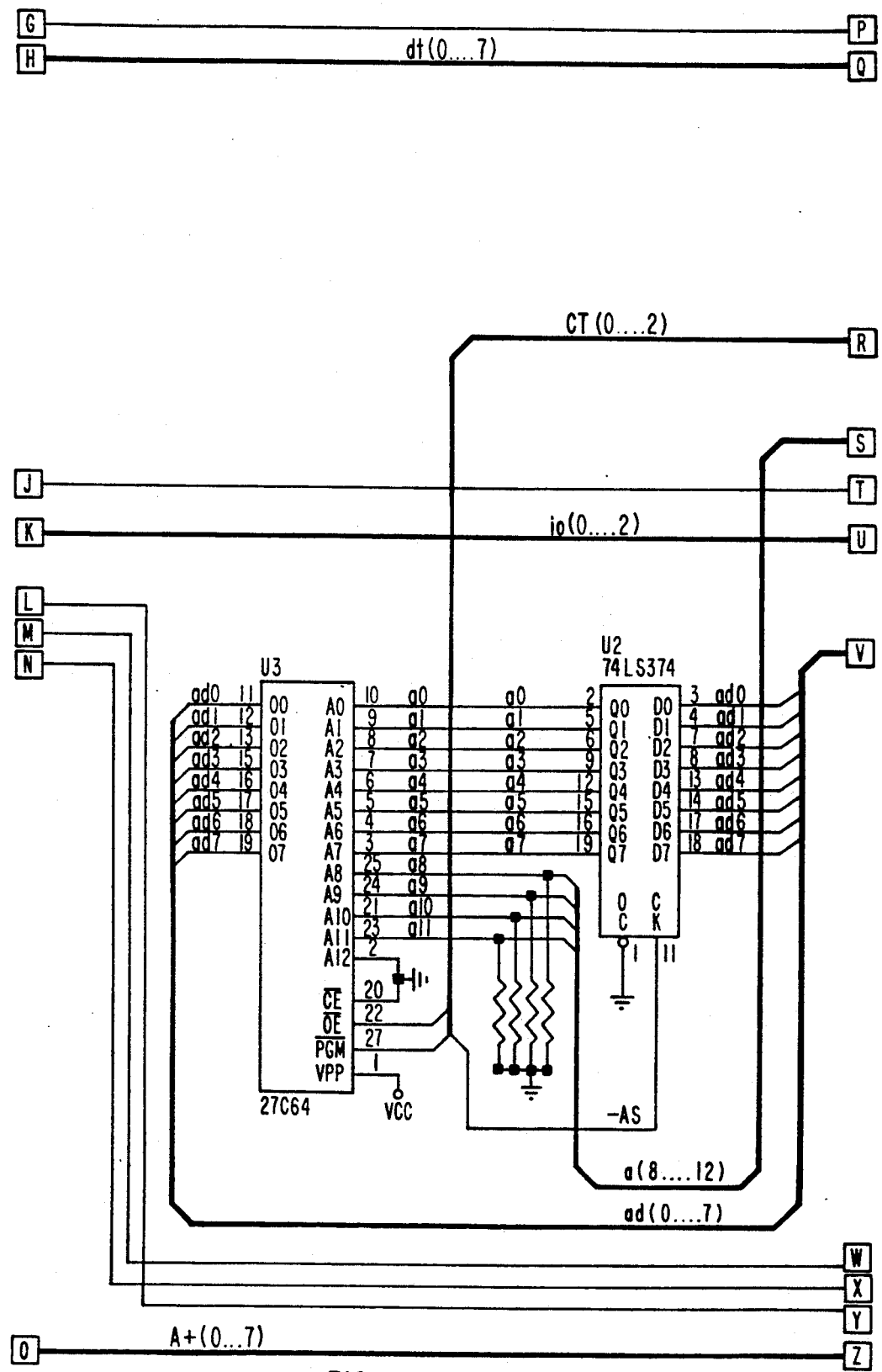
Figure 4D:
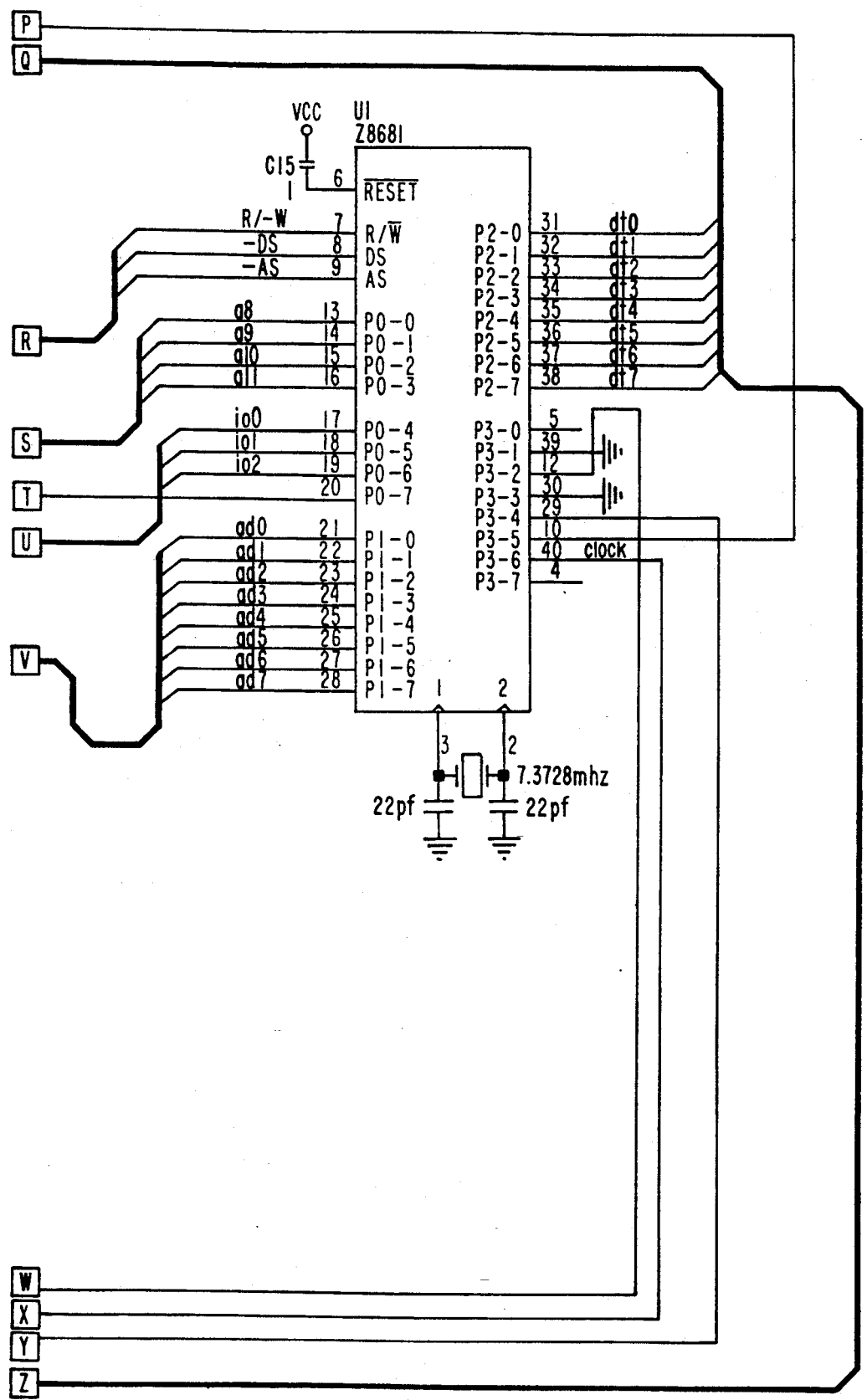
Figure 4E:
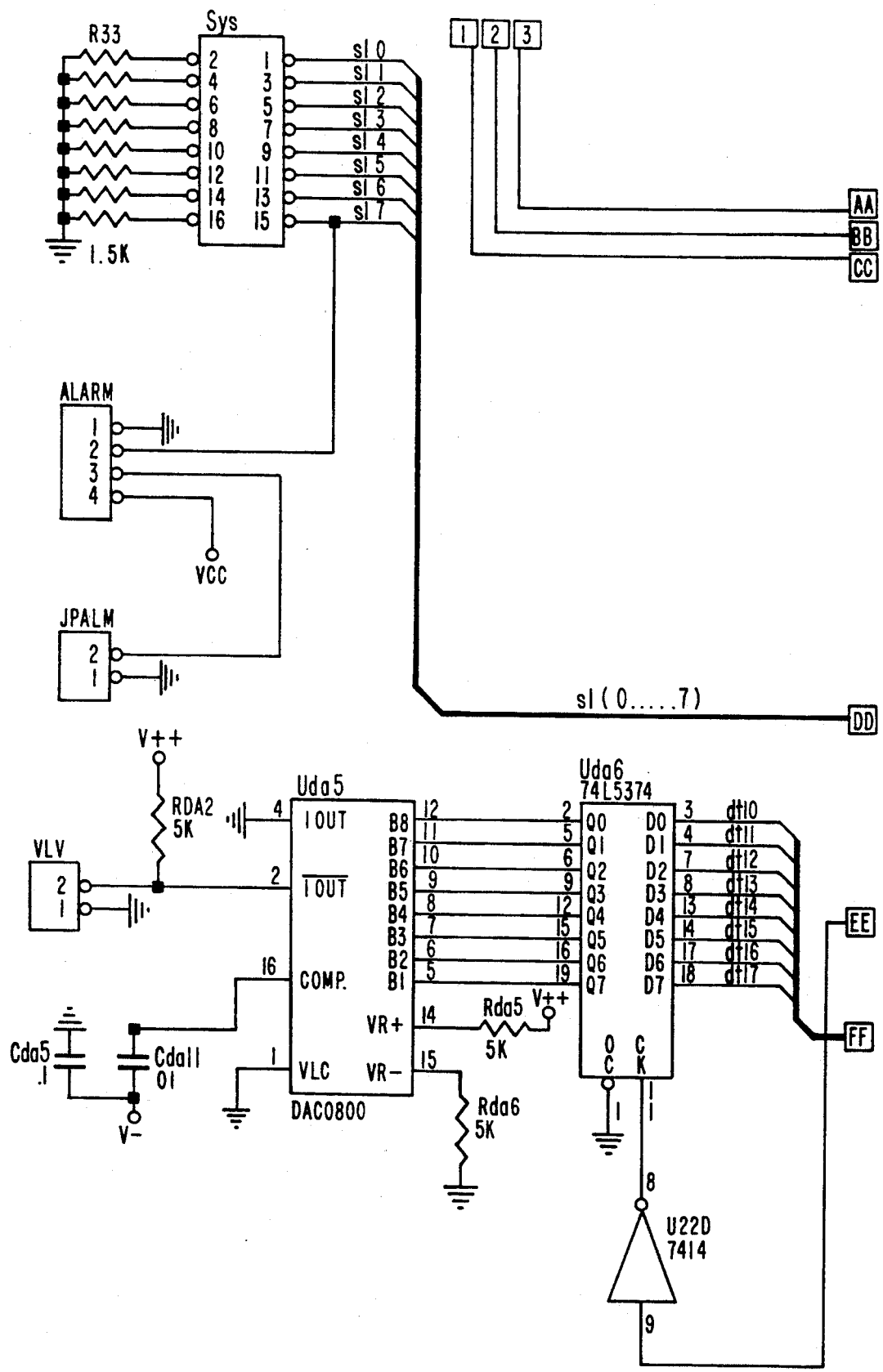
Figure 4F:
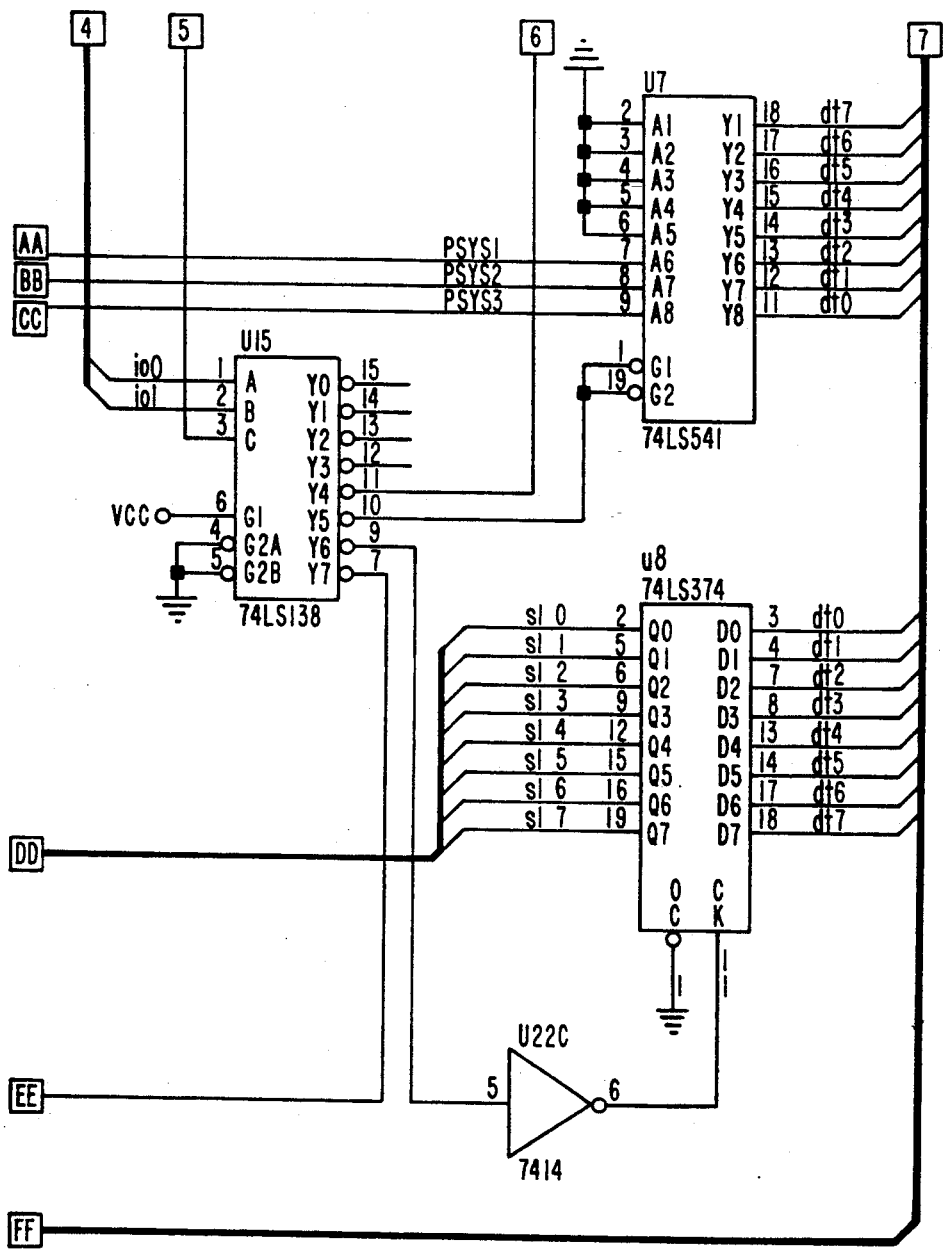
Figure 4F:
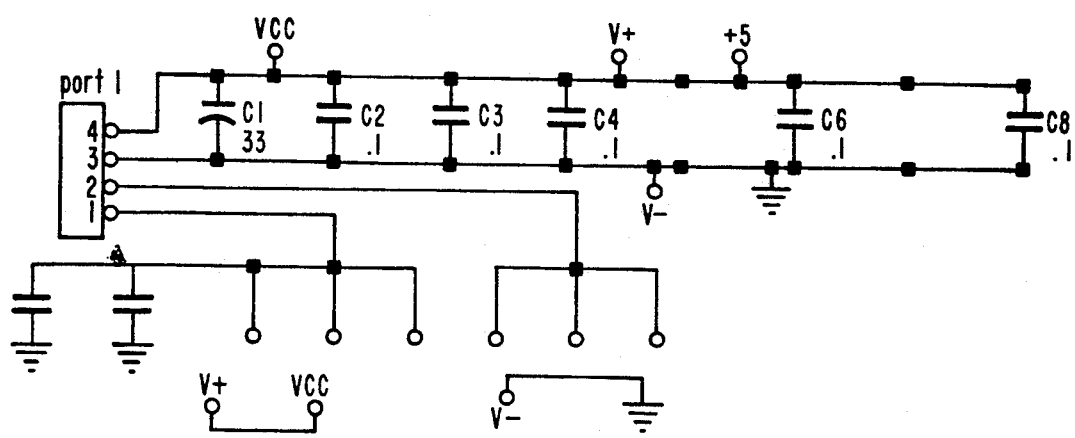

FIG. 3 is a diagram showing the arrangement of another apparatus which may be used to manually carry out the method of the present invention. Represented in FIG. 3 is a tank 300 containing pressurized gas. A pressure regulator 302 is manually changed to increase or decrease the pressure of the gas leaving the tank 300 and the pressure at the inlet of the membrane gas exchange device 312. Flow control valve 304 is manually adjusted to maintain the desired gas flow into the gas exchange device 312. The pressure gauges 306 and 316 measure the pressure at the inlet and the outlet of the membrane gas exchange device 312. Relief valves 308A-B and filter 310 are positioned upstream from the membrane gas transfer device 312. A liquid trap 314 is positioned immediately downstream from the membrane gas exchange device. Another flow control valve 318, positioned immediately upstream from the vacuum pump 320, is adjusted to set the flow through the membrane gas exchange device 312 to the desired value.

FIGS. 4A-4F provide detailed schematic diagrams of the presently preferred circuit implementation of the central controller 130 which may be included in the present invention. It will be appreciated that the circuit represented in FIGS. 4A-4F is merely exemplary of the arrangements and devices which can be incorporated into the present invention. Also, the boxed designations shown in FIGS. 4A-4F indicate the circuit interconnections between the figures.

Provided below in Table A is a list of the parts referenced in FIGS. 4A-4F. The reference designations included in FIGS. 4A-4F are those which are commonly used in the art in such schematic diagrams.

TABLE A

| Item | Quantity | Reference Designation | Part No. |
|------|----------|----------------------|----------|
| 1 | 4 | u6, U2, Uda6, u8 | 74LS374 |
| 2 | 1 | U1 | Z8681 |
| 3 | 1 | U4 | ADC0808 |
| 4 | 1 | U15 | 74LS138 |
| 5 | 1 | U7 | 74LS541 |
| 6 | 1 | U9 | 741 |
| 7 | 1 | XSTL | 7.3728 mhz |
| 8 | 1 | U3 | 27C64 |
| 9 | 1 | C1 | 33 |

TABLE A-continued

| Item | Quantity | Reference Designation | Part No. |
|---|---|---|---|
| 10 | 4 | Psys, f1, f2, Sys | |
| 11 | 7 | R33, R34, R35, R36, R37, R38, R40 | RESISTOR |
| 12 | 2 | R66, R104 | 50 k |
| 13 | 2 | U5, Uda5 | DAC0800 |
| 14 | 8 | C2, C3, C4, C5, Cda5, C6, C7, C8 | .1 |
| 15 | 2 | C9, C10 | 22 pf |
| 16 | 2 | C11, Cda11 | 01 |
| 17 | 1 | port1 | |
| 18 | 1 | C15 | 1 |
| 19 | 1 | JP20 | |
| 20 | 4 | R4, R1, R2, R3 | 10K |
| 21 | 1 | U22 | 7414 |
| 22 | 1 | RDA | 2.5K |
| 23 | 2 | R5, R6 | 2.5 k |
| 24 | 3 | R42, R43, R44 | 10 k |
| 25 | 1 | ALARM | |
| 26 | 1 | R41 | 1.5K |
| 27 | 2 | JPALM, VLV | |
| 28 | 1 | RLED | |
| 29 | 2 | P2, P1 | |
| 30 | 1 | RPWR | |
| 31 | 3 | RDA2, Rda5, Rda6 | 5K |
| 32 | 1 | Cda7 | 0.1 |

In view of the foregoing, it will be appreciated that the present invention provides a blood gas exchange delivery system which is safer to use than previous available manual or automatic ventilatory gas delivery systems and which maintains more efficient oxygen and carbon dioxide transfer with the blood than previously known devices. The present invention also advantageously maintains the gas phase pressure within the gas permeable membrane gas exchange device at a pressure below the central venous pressure of the patient to ensure that formation of gas emboli in the blood does not occur. Moreover, embodiments of the present invention may be easily set up and operated for long periods of time without constant attention from a technician.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

United States Patent Application of

Gaylord Berry and

Yansong Shan for

AUTOMATED GAS DELIVERY SYSTEM
FOR
BLOOD GAS EXCHANGE DEVICES

PROGRAMMING CODE APPENDIX

Copyright 1990 CardioPulmonics, Inc.

```
SYSTEM>>
   SUBTITLE   <<CONTROL>>
   SYNTAX     2500

;----------------MISC. EQUATES

FALSE        EQU 00
TRUE         EQU .NOT.FALSE

BELL         EQU 07           ;BELL CODE
CR     EQU 'CR'
LF     EQU 'LF'
SP     EQU 'SP'
HT     EQU 'HT'
NL     EQU 'NL'

CLOCK        EQU 7373

USEC         EQU CLOCK/7373   ;1-5 USEC DELAY
MSEC         EQU CLOCK/35     ;1 MSEC

CONSTANT
   DAC0800:    EQU   10000000B
   USER_INTF:        EQU   10000000B
   SYS_OUT:    EQU   10000000B
   PS1:        EQU   182
   PS2:        EQU   70
   PS3:        EQU   170
   ALPHA:            EQU   4      ;INVERSE
   THRESHOLD:        EQU   10
   P_ATM:            EQU   178    ;3.5V
   C_VALVE:    EQU   50
   K_ADAPT:    EQU   1      ;LEARNING CONSTANT
   R_FLOW:     EQU   100
   P_WANT:     EQU   170    ;APPROX. 3V
   MAX_VAC:    EQU   255    ;APPROX. 5V

RATE_F:     EQU   20     ;SOFTWARE DEPENDENT

EOC:        EQU   00000001B
   STACK:            EQU   7FH

P0:         REG   R0
   P1:         REG   R1
   P2:         REG   R2
   P3:         REG   R3

RG0:        REG   R4    ;
   RG1:        REG   R5    ;
   RG2:        REG   R6    ;
   RG3:        REG   R7    ;
   RG4:        REG   R8    ;
   RG5:        REG   R9    ;
   RG6:        REG   R10   ;
   RG7:        REG   R11   ;
```

```
RG8:         REG   R12   ;TEMPORARY AD/DA STORE
RG9:         REG   R13
RG10:              REG   R14   ;USED FOR TIME DELAY
RG11:              REG   R15   ;USED FOR TIME DELAY

RG45:              REG   RR8   ;REG PAIR 4&5

LEDS:              REG   MR16  ;LED REGISTER
AD0:         REG   MR17  ;AD CHANNEL #0
AD1:         REG   MR18  ;AD CHANNEL #1
AD2:         REG   MR19  ;AD CHANNEL #2
AD6:         REG   MR20  ;AD CHANNEL #6
AD7:         REG   MR21  ;AD CHANNEL #7

FLOW1:             REG   MR22  ;FLOW #1
FLOW2:             REG   MR23  ;FLOW #2
PRESSURE_IN:       REG   MR24  ;INLET PRESSURE
PRESSURE_OUT:      REG   MR25  ;OUTLET PRESSURE

DAVAL_F:     REG   MR26  ;CURRENT DA VALUE FLOW
DAVAL_P:     REG   MR27  ;CURRENT DA VALUE PRESSURE
ALARM:             REG   MR28  ;ALARM CLEAR/SET
ERR_P:             REG   MR29  ;PRESSURE ERROR
ALPHA_HI:    REG   MR30  ;ALPHA REGISTER - 16 BIT
ALPHA_LO:    REG   MR31
COUNT:             REG   MR32  ;LOOP COUNTER
VOUT:              REG   MR33  ;OUTPUT REGISTER
F2_C:              REG   MR34  ;COMMAND TO F2
DF2:         REG         MR35
DF1:         REG   MR36
RG_F:              REG   MR37

IRQ0:        DW    START
IRQ1:        DW    START
IRQ2:        DW    START
IRQ3:        DW    START
IRQ4:        DW    START
IRQ5:        DW    START

ORG  000CH
    JP   START
START:
;(1) SET UP INTERRUPTS
    CLR  RP
    LD   IPR,#0BH
    CLR  IMR
    CLR  IRQ
    EI
    DI

;(2) INITIALIZE REGISTER POINTER AND STACK
    LD   SPL,#STACK

;(3) INITIALIZE I/O PORTS
    LD   P2M,#0FFH

;         SERIAL I/O
```

```
        CLR   SIO
        LD    PRE0,#00001101B
        LD    T0,#2              ;9600 BAUD
        LD    P3M,#01000001B

;(4) INITIALIZE COUNTER/TIMER
        LD    PRE1,#00000111B
        LD    T1,#01H

LD    TMR,#10001111B

AND   FLAGS,#0FCH        ;RESET FLAGS
        CLR   FLOW1              ;INIT.
        CLR   FLOW2
        CLR   ALPHA_HI
        CLR   ALPHA_LO
        LD    PRESSURE_IN,P_ATM
        LD    PRESSURE_OUT,#50

LD    DAVAL_F,#0FFH      ;CLEAR USER INTRFACE
        LD    DAVAL_P,#0FFH
        CALL  DA_OUT_F
        CALL  DA_OUT_P
        CLR   LEDS               ;CLEAR LEDS
        CALL  LED
        CLR   ALARM
        LD    COUNT,RATE_F
        LD    VOUT,100

CHK_TEST:
        CALL  SWITCH             ;CHK. FOR TEST MODE
        TM    RG0,#04H           ;BIT 2
        JP    NZ,MENU            ;BRANCH IF TEST MODE

;---------------CHECK USER INTERFACE

WORKING:
        CALL  LED                ;DISPLAY LEDS AND ALARM
        CLR   LEDS               ;RESET REG.
        CALL  ADAPT_F            ;CHK. USER INTERFACE
;       CALL  ADAPT_P

LD    RG0,DAVAL_F
        COM   RG0
        CALL  HEX_ASC
        CALL  SPACE

;--------------READ IN PRESSURE AND FLOW

LD    RG9,#00H           ;CHAN #0 (PRESSURE_IN)
        CALL  AD_IN
        LD    AD0,RG0            ;SAVE IT
        LD    PRESSURE_IN,RG0

LD    RG9,#10H           ;CHAN #1 (PRESSURE_OUT)
```

```
        CALL AD_IN
        LD   AD1,RG0      ;SAVE IT
        LD   PRESSURE_OUT,RG0

LD   RG9,#20H     ;CHAN #2
        CALL AD_IN
        LD   AD2,RG0      ;SAVE IT
        LD   F2_C,AD2

LD   RG9,#60H     ;CHAN #6 (FLOW1)
        CALL AD_IN
        LD   AD6,RG0      ;SAVE IT
        LD   FLOW1,RG0

LD   RG9,#70H     ;CHAN #7 (FLOW2)
        CALL AD_IN
        LD   AD7,RG0      ;SAVE IT
        LD   FLOW2,RG0

;---------------ADAPTIVE CONTROL

CP   PRESSURE_IN,P_WANT
        JR   UGE,DECV
        LD   ERR_P,P_WANT
        SUB  ERR_P,PRESSURE_IN
        ADD  VOUT,ERR_P
        JR   C,OV1
        JR   ALFA
OV1:    LD   VOUT,0FFH
        JR   ALFA
DECV:   LD   ERR_P,PRESSURE_IN
        SUB  ERR_P,P_WANT
        SUB  VOUT,ERR_P
        JR   C,ZERO1
        JR   ALFA
ZERO1:  LD   VOUT,00H
ALFA:
        LD   DAVAL_P,VOUT    ;SAVE IF OKAY
        COM  DAVAL_P
        CALL DA_OUT_P  ;CHANGE D TO A

CALL    IN_CHK
        CALL SORS_CHK
        CALL VCP_CHK
        JP   CHK_TEST

;----------------COMPARE TO STANDARD VALUES

CP   AD0,PS1     ;CHK PRESSURE #1
        JR   ULE,CMP1    ;BRANCH OKAY

OR   LEDS,#81H ;SET ALARM AND LED 1

CMP1:   CP   AD1,PS2     ;CHK. PRESSURE #2
        JR   ULE,CMP2    ;BRANCH OKAY

OR   LEDS,#82H ;SET ALARM AND LED 2
```

```
CMP2:    CP   AD2,PS3    ;CHK. PRESSURE #3
   JR   ULE,FLOW   ;BRANCH OKAY

OR   LEDS,#84H  ;SET ALARM AND LED 3

;---------------CHK. FLOW VALUES

FLOW:    LD   RG0,FLOW2  ;GET FLOW1
   SUB  RG0,FLOW1  ;GET DELTA
   JR   NC,FL1              ;BRANCH FLOW2 GTE FLOW1

OR   LEDS,#88H  ;SET ALARM
   JP   CHK_TEST   ;LOOP

FL1:     PUSH RG0           ;SAVE DELTA
   LD   RG0,FLOW1  ;LOAD DIVIDEND
   CLR  RG1
   LD   RG2,ALPHA  ;LOAD DIVISOR
   CALL DIVIDE            ;RESULTS IN RG1

POP  RG0        ;RESTORE DELTA TO RG0
   SUB  RG0,RG1    ;CHK. DIFFERENCE
   JR   EQ,FL2             ;BRANCH OKAY

CP   RG0,#THRESHOLD ;TEST ABSOLUTE DIFFERENCE
   JR   ULE,FL2    ;BRANCH OKAY
   LD   LEDS,#88H  ;SET ALARM

FL2:     JP   CHK_TEST

;------------------TEST ROUTINE

MENU:    CALL PROMPT

M0: CALL SWITCH             ;CHK. FOR TEST MODE
    TM   RG0,#04H
    JP   Z,CHK_TEST         ;LOOP NOT TEST MODE

CALL SIO_IN
    JR   Z,M0

LD   RG4,#>MENU         ;RETURN ADDR.
    LD   RG5,#<MENU
    PUSH RG5
    PUSH RG4

AND  RG0,#.NOT.20H   ;MAKE UPPER CASE

CP   RG0,#'S'   ;SELECT A/D CHANNEL
    JP   Z,SEL_AD

CP   RG0,#'U'   ;USER S/W INTERFACE
    JP   Z,USER_IN
```

```
        CP    RG0,#'L'    ;ACTIVATE LED'S
        JP    Z,CHK_LED

ERROR:  CALL CR_LF        ;RESET CURSOR

LD    RG0,#BELL   ;ERROR
        CALL  SIO_OUT     ;SEND BELL CODE
        RET

SEL_AD:
        CALL SIO_IN        ;GET CHANNEL #
        JR   Z,SEL_AD      ;LOOP TIL THERE

CP   RG0,#'A'      ;DISPLAY ALL
        JP   NZ,SEL1       ;BRANCH NOT ALL

SEL2:   LD   RG9,#00H     ;CHAN #0 (PRESSURE_IN)
        CALL AD_IN
        LD   AD0,RG0      ;SAVE IT
        LD   PRESSURE_IN,RG0

LD   RG9,#10H     ;CHAN #1 (PRESSURE_OUT)
        CALL AD_IN
        LD   AD1,RG0      ;SAVE IT
        LD   PRESSURE_OUT,RG0

LD   RG9,#20H     ;CHAN #2
        CALL AD_IN
        LD   AD2,RG0      ;SAVE IT

LD   RG9,#60H     ;CHAN #6 (FLOW1)
        CALL AD_IN
        LD   AD6,RG0      ;SAVE IT
        LD   FLOW1,RG0

LD   RG9,#70H     ;CHAN #7 (FLOW2)
        CALL AD_IN
        LD   AD7,RG0      ;SAVE IT
        LD   FLOW2,RG0

LD   RG0,AD0
        CALL HEX_ASC
        CALL SPACE

LD   RG0,AD1
        CALL HEX_ASC
        CALL SPACE

LD   RG0,AD2
        CALL HEX_ASC
        CALL SPACE

LD   RG0,AD6
        CALL HEX_ASC
        CALL SPACE
```

```
        LD    RG0,AD7
        CALL  HEX_ASC
        CALL  SPACE

LD    RG0,DAVAL_F
        COM   RG0
        CALL  HEX_ASC
        CALL  SPACE

LD    RG0,DAVAL_P
        COM   RG0
        CALL  HEX_ASC
        CALL  SPACE

CALL  SIO_IN            ;CHK. FOR TERMINATION
        JR    Z,SEL2             ;LOOP TIL TERMINATED
        CALL  CR_LF_LF

RET

SEL1:   AND   RG0,#07H    ;TAKE LOWER 3 BITS
        SWAP  RG0          ;MOVE UP
        LD    RG9,RG0      ;HOLD IT

SEL0:   CALL  AD_IN             ;SELECT A/D
        CALL  HEX_ASC
        CALL  SPACE

CALL  SIO_IN            ;CHK. FOR TERMINATION
        JR    Z,SEL0             ;LOOP TIL TERMINATED

CALL  CR_LF_LF

RET

IN_CHK:
        CP    PRESSURE_IN,PS1         ;COMPARE INLET PRESSURE
        JR    ULE,ENDIN        ;BENCH END IF OK
        CP    PRESSURE_OUT,PS2   ;COMPARE OUTLET PRESSURE
        JR    UGT,IN1              ;OUTLET OK THEN INLET PROBLEM
        OR    LEDS,#84H        ;SET OUTLET SIGNAL
        JR    ENDIN                ;END
IN1:    OR    LEDS,#88H        ;INLET SIGNAL
ENDIN:  RET

SORS_CHK:
        CP    F2_C,FLOW2
        JR    UGT,SRS1
        LD    DF2,FLOW2
        SUB   DF2,F2_C
        JR    SRS2
SRS1:   LD    DF2,F2_C
        SUB   DF2,FLOW2
SRS2:   CP    DF2,#30H
        JR    ULT,SRS3
        OR    LEDS,#81H
SRS3:   RET
```

```
VCP_CHK:
    LD    RG_F,DAVAL_F
    COM   RG_F
    CP    FLOW1,RG_F
    JR    UGE,VPC3
    LD    DF1,RG_F
    SUB   DF1,FLOW1
    CP    DF1,#03H
    JR    ULE,VPC3
    OR    LEDS,#10H
    CP    PRESSURE_OUT,PS2
    JR    UGE,VPC3
    OR    LEDS,#82H
VPC3    RET

;------------------USER INTERFACE

USER_IN:
    CALL SIO_IN          ;CHK. FLOW OR PRESSURE
    JR   Z,USER_IN       ;LOOP TIL THERE

CP   RG0,#'F'        ;CHK. IF FLOW
    JR   Z,USE1          ;BRANCH IF FLOW

CP   RG0,#'P'        ;CHK. IF PRESSURE
    JR   Z,USE2          ;BRANCH IF PRESSURE

JP   ERROR           ;ERROR

USE1:   AND  LEDS,#7FH   ;RESET ALARM
    CALL LED

CALL USER_F          ;CHK. USER INTERFACE

CALL SIO_IN          ;CHK. TERMINATION
    JR   Z,USE1          ;LOOP NO TERMINATION

CALL CR_LF_LF        ;RESET CURSOR

RET

USE2:   AND  LEDS,#7FH   ;RESET ALARM
    CALL LED

CALL USER_P          ;CHK. USER INTERFACE

CALL SIO_IN          ;CHK. TERMINATION
    JR   Z,USE2          ;LOOP NO TERMINATION

CALL CR_LF_LF        ;RESET CURSOR

RET

;------------------------------------------------
```

```
CHK_LED:
    CALL SIO_IN         ;GET LED #
    JR   Z,CHK_LED      ;LOOP TIL THERE

AND  RG0,#07H       ;TAKE LOWER 3 BITS
    INC  RG0

CLR  LEDS
    SCF

CHK1:   RLC  LEDS
    DJNZ RG0,CHK1       ;LOOP TIL SET

CALL LED            ;SELECT A/D

CALL CR_LF_LF

RET
;----------------------------------------------

;----------D TO A FLOW

USER_F: CALL  SWITCH        ;GET SWITCH SETTINGS
    AND  RG0,#03        ;ONLY BITS 0 AND 1
    JR   Z,USER0        ;BRANCH IF ZERO

CP   RG0,#3         ;CHK. FOR BOTH CLOSED
    JR   NZ,USER2
    OR   LEDS,#80H      ;SET ALARM BIT
    CALL LED

JR   USER0

USER2:  CP   RG0,#1         ;CHK. BIT 0
    JR   NZ,USER1       ;BRANCH TO NEXT TEST

CP   DAVAL_F,#FFH   ;CHK. IF ALREADY FFH
    JR   Z,USER0        ;BRANCH IF SO
    INC  DAVAL_F        ;IF SO, INCREMENT
    JR   USER0          ;BRANCH TO EXIT

USER1:  CP   RG0,#2         ;CHK. BIT 1
    JR   NZ,USER0       ;BRANCH TO EXIT
    CP   DAVAL_F,#00    ;CHK. IF ALREADY 00H
    JR   Z,USER0        ;BRANCH IF SO

DEC  DAVAL_F        ;IF SO, DECREMENT

USER0:  CALL DA_OUT_F       ;LOAD D TO A

LD   RG0,DAVAL_F    ;DISPLAY IT
    COM  RG0
    CALL HEX_ASC
    CALL SPACE

LD   RG2,#100       ;DELAY 1/10 SEC
    CALL DELAY1MS
```

```
        RET

;-------------- FLOW OUT USED IN ADAPT LOOP --------------
ADAPT_F:
    CALL SWITCH            ;GET SWITCH SETTINGS
    AND  RG0,#03    ;ONLY BITS 0 AND 1
    JR   NZ,ADPTF4         ;BRANCH IF NON-ZERO
    RET

ADPTF4: DEC  COUNT              ;INC. LOOP COUNTS
    JR   Z,ADPTF5
    RET

ADPTF5: LD   COUNT,RATE_F
    CP   RG0,#3          ;CHK. FOR BOTH CLOSED
    JR   NZ,ADPTF2
    OR   LEDS,#80H  ;SET ALARM BIT
    CALL LED

JR   ADPTF0

ADPTF2: CP   RG0,#1          ;CHK. BIT 0
    JR   NZ,ADPTF1 ;BRANCH TO NEXT TEST

CP   DAVAL_F,#FFH    ;CHK. IF ALREADY FFH
    JR   Z,ADPTF0  ;BRANCH IF SO
    INC  DAVAL_F   ;IF SO, INCREMENT
    JR   ADPTF0            ;BRANCH TO EXIT

ADPTF1: CP   RG0,#2          ;CHK. BIT 1
    JR   NZ,ADPTF0 ;BRANCH TO EXIT
    CP   DAVAL_F,#00     ;CHK. IF ALREADY 00H
    JR   Z,ADPTF0  ;BRANCH IF SO

DEC  DAVAL_F   ;IF SO, DECREMENT

ADPTF0: CALL DA_OUT_F  ;LOAD D TO A

RET

;------------ PRESSURE OUT IN ADAPT LOOP -----------
ADAPT_P:

CALL DA_OUT_P  ;LOAD D TO A
    RET

;------------D TO A PRESSURE

USER_P: CALL  SWITCH           ;GET SWITCH SETTINGS
    AND  RG0,#03    ;ONLY BITS 0 AND 1
    JR   Z,USERP0  ;BRANCH IF ZERO

CP   RG0,#3          ;CHK. FOR BOTH CLOSED
    JR   NZ,USERP2
    OR   LEDS,#80H  ;SET ALARM BIT
    CALL LED
```

```
        JR    USERP0

USERP2: CP    RG0,#1          ;CHK. BIT 0
        JR    NZ,USERP1 ;BRANCH TO NEXT TEST

CP    DAVAL_P,#FFH    ;CHK. IF ALREADY FFH
        JR    Z,USERP0  ;BRANCH IF SO
        INC   DAVAL_P   ;IF SO, INCREMENT
        JR    USERP0          ;BRANCH TO EXIT

USERP1: CP    RG0,#2          ;CHK. BIT 1
        JR    NZ,USERP0 ;BRANCH TO EXIT
        CP    DAVAL_P,#00     ;CHK. IF ALREADY 00H
        JR    Z,USERP0  ;BRANCH IF SO

DEC   DAVAL_P   ;IF SO, DECREMENT

USERP0: CALL  DA_OUT_P  ;LOAD D TO A

LD    RG0,DAVAL_P     ;DISPLAY IT
        COM   RG0
        CALL  HEX_ASC
        CALL  SPACE

LD    RG2,#100  ;DELAY 1/10 SEC
        CALL  DELAY1MS

RET

;----------------------------------------

DA_OUT_F:
        LD    P2M,#00000000B ;SET TO OUTPUTS

CLR   P0            ;SETS U6 CK LOW
        LD    P2,DAVAL_F    ;LOAD DATA
        COM   P2
        LD    P0,#10000000B ;LATCH DATA IN U6
        RET

DA_OUT_P:
        LD    P2M,#00000000B ;SET TO OUTPUTS

CLR   P0            ;SETS UDA6 CK LOW
        LD    P2,DAVAL_P    ;LOAD DATA
        COM   P2
        LD    P0,#10110000B ;LATCH DATA IN UDA6
        RET

USER_ITFS
        LD    P2M,#11111111B
        LD    P0,SYS_OUT
        LD    R6,P2
        RET

;---------------------------------------------
```

```
;       CALL   RG9 = CHANNEL #

;       RET    RG0 = VALUE

AD_IN:
        LD      P2M,#11111111B  ;SET DATA PORT AS INPUT
        LD      P0,RG9          ;SET A/D TO CHANNEL 0

OR      P3,#00010000B   ;RESET A/D
        AND     P3,#11101111B   ;ENABLE CONVERSION
        LD      RG2,#40
        CALL    DELAY

WAIT:   TM      P3,#04H         ;WAIT FOR E-O-CONVERSION
        JR      Z,WAIT          ;LOOP

OR      P3,#00100000B   ;ENABLE A/D OUTPUT
        LD      RG0,P2          ;SAVE A/D VALUE
        AND     P3,#11011111B   ;DISABLE A/D OUTPUT

RET

;------------------------------------------------------------

;       CALL:   LEDS = LED BIT PATTERN

;       RET:    LEDS = UNCHANGED

LED:    CLR     P0
        LD      P2M,#00000000B  ;SET TO OUTPUTS
        LD      P2,LEDS

LD      P0,#10100000B   ;LATCH DATA IN U8
        CLR     P0

RET                     ;DONE

;------------------------------------------------------------

;       CALL:   NONE

;       RET:    RG0 = SWITCH BLOCK BYTE, BITS 3-7 = 00000

SWITCH: LD      P2M,#0FFH       ;SET TO INPUTS
        LD      P0,#10010000B   ;OPEN UP U7 TRI-STATE
        LD      RG0,P2          ;GET S/W SETTINGS
        CLR     P0              ;SET U7 TRI-STATES
        AND     RG0,#00000111B  ;CLEAR BITS 3-7

RET

;------------------------------------------------------------

;       CALL:   RG0 = BIT NUMBER
```

```
;    RET: RG0 = BIT SET

SET_BIT:
    LD    RG6,RG0    ;SET LOOP COUNTER
    CLR   RG0        ;RESET RG0
    SCF              ;LOAD CARRY FLAG

BIT0:   RLC RG0       ;ROTATE CARRY BIT
    DJNZ RG6,BIT0    ;LOOP TIL BIT POSITIONED

RET

;------------------------------------------------

SUBTITLE  ( SUBROUTINES )
    PAGE

;------------------------------------------------

SUBTITLE  ( UTILITIES )
    PAGE

;------------------------------------------------
;           UTILITIES
;------------------------------------------------

ORG   600H

;------------------------------------------------
;------------------------------------------------
;   -BYTE OUTPUT ROUTINE
;   CALL:    REG. RG0 = OUTPUT BYTE
;   RET: REG. RG0 = OUTPUT BYTE

SIO_OUT:
    TM    IRQ,#10H   ;CHK. IF EMPTY
    JR    Z,SIO_OUT  ;LOOP IF NOT EMPTY

AND   IRQ,#EFH   ;CLEAR EMPTY BIT
    LD    SIO,RG0    ;SEND BYTE

RET              ;DONE

;----------------CHARACTER INPUT ROUTINE

;         CALL:    NONE

;         RET: REG. RG0 = CHARACTER
;              Z-FLAG SET = NO CHAR
;              Z-FLAG CLEAR = CHAR. AVAIL.
```

```
SIO_IN:  TM    IRQ,#08H    ;CHK. IF FULL
         JR    Z,IN0       ;BRANCH NO DATA

PUSH  FLAGS
         AND   IRQ,#F7H    ;CLEAR FULL BIT
         LD    RG0,SIO     ;GET BYTE
         AND   RG0,#7FH    ;CLEAR PARITY

IN2:     CALL  SIO_OUT     ;SET Z-FLAG, CHAR. AVAIL.
         POP   FLAGS

IN0:     RET               ;CONTINUE SIO IN TEST

;-------------------------------------------------------------

;    1-5 USEC DELAY ROUTINE

;    REG. RG2 = NUMBER OF USECS
;    USES REGISTER RG3

DELAY:   CP    RG2,#0
         JR    Z,DLY2      ;NO DELAY, GO AROUND

DLY3:    LD    RG3,#USEC   ;500 USEC LOOP TIME
DLY1:    NOP               ;WASTE TIME
         DJNZ  RG3,DLY1    ;DELAY 500 USEC
         DEC   RG2         ;ADJ. COUNT
         JR    NZ,DLY3     ;LOOP TIL DONE

DLY2:    RET

;-------------------------------------------------------------

;    1 MSEC DELAY ROUTINE

;    REG. RG2 = NUMBER OF MSECS
;    USES REGISTER RG3

DELAY1MS:
         CP    RG2,#0
         JR    Z,DLYM2     ;NO DELAY, GO AROUND

DLYM3:   LD    RG3,#MSEC   ;1 MSEC LOOP TIME
DLYM1:   NOP               ;WASTE TIME
         DJNZ  RG3,DLYM1   ;DELAY 1 MSEC

DEC   RG2         ;ADJ. COUNT
         JR    NZ,DLYM3    ;LOOP TIL DONE

DLYM2:   RET

;----------------CURSOR RESET

CR_LF_LF:
```

```
        LD    RG0,#'LF'   ;SEND LF
        CALL SIO_OUT
        LD    RG2,#20     ;DELAY 10 MSEC
        CALL DELAY

CR_LF:  LD    RG0,#'LF'   ;SEND TWO LF'S
        CALL SIO_OUT
        LD    RG2,#20     ;DELAY 10 MSEC
        CALL DELAY

CRET:   LD    RG0,#'CR'   ;SEND CR
        CALL SIO_OUT
        LD    RG2,#20     ;DELAY 10 MSEC
        CALL DELAY

RET               ;DONE

;-----------------DISPLAY ONE SPACE

SPACE:  LD    RG0,#'SP'   ;LOAD SPACE
        CALL SIO_OUT

RET               ;DONE

;-----------------OUTPUT PROMPT

PROMPT: LD    RG0,#'>'    ;LOAD PROMPT
        CALL SIO_OUT
        RET

;-----------------TEST ROUTINE   HEX TO ASCII

;   CALL:    REG. RG0 = HEX DATA
;   RET:  REG. RG0 = SPACE

HEX_ASC:
        PUSH RG0          ;SAVE DATA
        SWAP RG0          ;UPPER NIBBLE

AND  RG0,#0FH     ;DISPLAY NIBBLE
        ADD  RG0,#90H
        DA   RG0
        ADC  RG0,#40H
        DA   RG0
        CALL SIO_OUT

POP  RG0          ;RESTORE
        AND  RG0,#0FH     ;DISPLAY LOWER
        ADD  RG0,#90H     ;NIBBLE
        DA   RG0
        ADC  RG0,#40H
        DA   RG0
        CALL SIO_OUT
```

```
        RET                     ;DONE

;---------------MULTIPLE 8 X 8

;   CALL:    REG RG2 = MULTIPLIER
;            REG RG5 = MULTIPLICAND
;            REG RG6 = LOOP COUNTER

;   RET: REG RG45 = PRODUCT

MULTIPLE:
    LD    RG6,#9           ;LOOP COUNTER
    CLR   RG4              ;INIT. HIGH RESULT BYTE
    RCF                    ;RESET ANY CARRY

MULT1:  RRC  RG4           ;HIGH PRODUCT
    RRC   RG5              ;LOW PRODUCT
    JR    NC,MULT2         ;BRANCH NO CARRY

ADD   RG4,RG2          ;COMBINE
MULT2:  DJNZ RG6,MULT1     ;LOOP TIL DONE

RET                    ;DONE

;---------------DIVIDE 16 / 8

;   CALL:    REG RG2 = 8 BIT DIVISOR
;            REG RG01 = 16 BIT DIVIDEND
;            REG RG6 = LOOP COUNTER

;   RET: REG RG1 = QUOTIENT
;            CARRY = 1 IF OVERFLOW

DIVIDE:
    LD    RG6,#8           ;LOOP COUNTER
    CP    RG2,RG0          ;? RESULTS IN 8 BITS
    JR    UGT,DIV1         ;BRANCH OKAY

LD    RG1,#0FFH        ;SHOW OVERFLOW
    SCF
    RET

DIV1:  RLC  RG1            ;DIVIDEND * 2
    RLC   RG0
    JR    C,DIV2           ;BRANCH OVERFLOW

CP    RG2,RG0
    JR    UGT,DIV3         ;CARRY = 0

DIV2:  SUB  RG0,RG2        ;DIVIDE
    SCF                    ;SHIFTED INTO RESULTS

DIV3:  DJNZ RG6,DIV1       ;LOOP, NO FLAGS AFFECTED

RLC   RG1              ;ADJ. CARRY, ALL DONE
    RET
```

```
        ORG     0F0CH
BOOT:   JP      $+3             ;LOAD UPPER 4 BITS
        LD      MR00,#0FH       ;INIT. PORT 0,0-3
        LD      P01M,#16H       ;INIT.
                                ;BIT 6-7 : OUTPUT P04-P07
                                ;BIT 5   : NORMAL
                                ;BIT 4-3 : AD0-AD7
                                ;BIT 2   : STACK INTERNAL
                                ;BIT 0-1 : A8-A11
        NOP                     ;LOAD PIPELINE
        NOP
        NOP
        JP      START           ;CONTINUE

END
```

What is claimed and desired to be secured by U.S. Letters Patent is:

1. A system for controlled delivery of gases from a pressurized gas source to a blood gas exchange device having a gas permeable membrane with a blood phase side in contact with blood to which the gas is to be transferred and with a gas phase side in contact with the gas, such that gas transfer to a patient's blood occurs across the membrane, the system comprising:

means for delivering gas under pressure from the gas source to the blood phase side of the gas permeable membrane of the gas exchange device; and means connected to said delivery means intermediate the gas source and the blood gas exchange device, for adjusting the pressure of the pressurized gas before it is delivered to the blood gas exchange device so as to limit the gas pressure at least in part by venting it external to the system to maintain the gas pressure delivered to the gas phase side of said membrane to a pressure that is below blood phase pressure occurring at the blood phase side of the membrane.

2. A system for controlling delivery of gases to a blood gas exchange device as defined in claim 1 wherein the means for adjusting the pressure comprises at least in part a pressure valve and the means for delivering a gas comprises a connector.

3. A system for controlled delivery of gases to a blood gas exchange device as defined in claim 1 wherein the means for adjusting the pressure of the gas comprises:

a pressure valve positioned upstream from the blood gas exchange device; and a vent to the atmosphere positioned in the gas stream between the means for delivering a gas and the pressure valve, the vent to the atmosphere venting any excess gas not allowed to continue in the gas stream to the blood gas exchange device by the pressure valve.

4. A system for controlled delivery of gases to a blood gas exchange device as defined in claim 3 further comprising a means for regulating the mass of the gas wherein the means for regulating the mass of the gas comprises a first mass flow controller.

5. A system for controlled delivery of gases to a blood gas exchange device as defined in claim 4 wherein the first mass flow controller is positioned in the gas flow downstream from the blood gas exchange device and wherein the system further comprising a second mass flow controller positioned in the gas flow between the vent and the means for receiving a gas.

6. A system for controlled delivery of gases to a blood gas exchange device as defined in claim 5 wherein the means for adjusting the pressure of the gas further comprises means for connecting to a source of vacuum positioned in the gas flow downstream from the second mass flow controller.

7. A system for controlled delivery of gases to a blood gas exchange device as defined in claim 6 further comprising control means for coordinating the operation of the first mass flow controller, the second mass flow controller, and the pressure valve.

8. A system for controlled delivery of gases to a blood gas exchange device as defined in claim 7 further comprising:

a first pressure sensor positioned to sense the pressure at the inlet of the blood gas exchange device;

a second pressure sensor positioned to sense the pressure at the outlet of the blood gas exchange device, the first and the second pressure sensors providing data to the control means; and a liquid trap positioned in the gas flow downstream from the blood gas exchange device.

9. A system for controlled delivery of gases to a blood gas exchange device as defined in claim 4 further comprising a central controller adapted for controlling the means for adjusting the pressure and the means for regulating the mass flow, the central controller comprising:

a microprocessor;

an analog to digital convertor; and a digital to analog convertor.

10. A system for controlled delivery of gases to a blood gas exchange device as defined in claim 9 further comprising a user interface, the user interface comprising:

a plurality of abnormal operating indicators;

a flow rate display; and a user operated flow rate input control.

11. A system for controlled delivery of gases to a blood gas exchange device as defined in claim 1 wherein a pressurized tank of gas serves as said pressurized gas source and a vacuum pump serving as a source of vacuum.

12. A system for controlled delivery of gases to a blood gas exchange device as defined in claim 1 wherein the means for adjusting the pressure of the gas received from the gas source comprises means for adjusting the a pressure at the gas permeable membrane to less than the patient's central venous pressure.

13. A system for controlled delivery of gases to a blood gas exchange device as defined in claim 1 wherein the means for adjusting the pressure of the gas received from the gas source comprises means for adjusting the a pressure at the gas permeable membrane to less than the ambient atmospheric pressure.

14. A system for controlled delivery of a gas from a pressurized gas source supplying gas at a pressure greater than a patient's central venous pressure to a membrane oxygenator having a gas permeable membrane with a blood phase side in contact with blood to which the gas is to be transferred and with a gas phase side in contact with the gas, such that gas transfer to a patient's blood occurs across the membrane, the system comprising:
   an inlet which is adapted to be connected to the pressurized gas source;
   flow control means for measuring and regulating the mass of the gas flowing through the membrane oxygenator from the gas source;
   means, connected intermediate the pressurized gas source and the gas permeable membrane for venting the gas to atmosphere so as to limit the gas pressure at least in part by venting it external to the system to maintain the gas pressure delivered to the gas phase side of the membrane to a pressure that is below blood phase pressure occurring at the blood phase side of the membrane;
   pressure control means for adjusting the pressure of the gas within the membrane oxygenator;
   an outlet which is adapted to be connected to a vacuum source for moving said gas flowing through said membrane oxygenator to said vacuum source, said outlet having a pressure which is less than the ambient atmospheric pressure; and
   central control means for operating the pressure control means and the flow control means such that the flow of the gas is sufficient to ensure gas transfer across the gas phase side of the membrane to the blood phase side of the membrane but without causing emboli to occur in the blood.

15. A system for delivering a gas to a membrane oxygenator which is capable of at least partially supporting the pulmonary function of a patient as defined in claim 14 wherein the flow control means comprises:
   inlet flow control means connected to the inlet of the membrane oxygenator; and
   outlet flow control means connected to the outlet of the membrane oxygenator.

16. A system for delivering a gas to a membrane oxygenator which is capable of at least partially supporting the pulmonary function of a patient as defined in claim 15 wherein the pressure control means is positioned in the gas flow between the inlet of the membrane oxygenator and the inlet flow control means and wherein an atmosphere vent is positioned in the gas flow between the pressure control means and the inlet flow control means.

17. A system for delivering a gas to a membrane oxygenator which is capable of at least partially supporting the pulmonary function of a patient as defined in claim 16 further comprising:
   an oxygenator inlet pressure sensor means positioned at the inlet of the membrane oxygenator; and
   an oxygenator outlet pressure sensor means positioned at the outlet of the membrane oxygenator.

18. A system for delivering a gas to a membrane oxygenator which is capable of at least partially supporting the pulmonary function of a patient as defined in claim 17 further comprising:
   a first bacteriological filter positioned in the gas flow on the inlet side of the membrane oxygenator; and
   a first liquid trap positioned in the gas flow on the outlet side of the membrane oxygenator.

19. A system for delivering a gas to a membrane oxygenator which is capable of at least partially supporting the pulmonary function of a patient as defined in claim 14 further comprising a vacuum pump serving as said source of vacuum.

20. A system for delivering a gas to a membrane oxygenator which is capable of at least partially supporting the pulmonary function of a patient as defined in claim 14 wherein the gas is a ventilatory gas.

21. A system for delivering a gas to a membrane oxygenator which is capable of at least partially supporting the pulmonary function of a patient as defined in claim 20 wherein the ventilatory gas is oxygen.

22. A system for delivering a gas to a membrane oxygenator which is capable of at least partially supporting the pulmonary function of a patient as defined in claim 14 wherein the membrane oxygenator is an intracorporeal membrane oxygenator.

23. A system for delivering a gas to the gas permeable membrane of a membrane oxygenator used to transfer oxygen into a patient's blood and carbon dioxide out of the patient's blood, the membrane oxygenator having an inlet and an outlet, the system being adapted for receiving a gas flow from a source of gas providing the gas at a higher than ambient pressure and being adapted for connection to a source of vacuum providing a pressure at lower than ambient pressure, the system comprising:
   a first mass flow controller adapted to be connected to the source of gas;
   a pressure valve positioned in the gas flow between the first mass flow controller and the gas permeable membrane of the membrane oxygenator;
   an atmospheric vent positioned in the gas flow between the pressure valve and the gas permeable membrane;
   a second mass flow controller adapted to be connected to the source of vacuum; and
   control means for controlling the first mass flow controller, the second mass flow controller, and the pressure valve such that there is sufficient gas flow at the gas permeable membrane to provide transfer of gases between the blood and the gas flow and such that the pressure of the gas within the membrane oxygenator at the gas permeable membrane is low enough that outgassing of the gas through the membrane as bubbles into the blood is avoided.

24. A system for delivering a gas to the gas permeable membrane of a membrane oxygenator used to transfer oxygen into the blood and carbon dioxide out of the blood as defined in claim 23 further comprising:

a first pressure sensor positioned to sense the pressure at the inlet of the membrane oxygenator;

a second pressure sensor positioned to sense the pressure at the outlet of the membrane oxygenator, the first and the second pressure sensors providing data to the control means; and a liquid trap positioned in the gas flow downstream from the membrane oxygenator.

25. A system for delivering a gas to the gas permeable membrane of a membrane oxygenator used to transfer oxygen into the blood and carbon dioxide out of the blood as defined in claim 23 wherein the control means comprises a microprocessor and wherein the system further comprises a user interface, the user interface comprising:

a plurality of abnormal operating indicators;

a flow rate display; and a user operated flow rate input control.

26. A system for delivering a gas to the gas permeable membrane of a membrane oxygenator used to transfer oxygen into the blood and carbon dioxide out of the blood as defined in claim 23 further comprising a pressurized tank of gas serving as a gas source and a vacuum pump serving as a source of vacuum.

27. A method of delivering a gas to a membrane oxygenator having an inlet and an outlet and adapted for at least partially supporting the pulmonary function of a patient, the method comprising the steps of:

receiving a flow of a gas from a gas source at a pressure higher than the ambient atmospheric pressure and directing the gas flow into the inlet of the membrane oxygenator;

adjusting the pressure of the gas flowing into the inlet of the membrane oxygenator to be below the blood phase pressure immediately adjacent to the membrane of the membrane oxygenator, at least in part by venting said gas external to the system before the gas is delivered to the membrane oxygenator, such that outgassing through the membrane is avoided; and regulating the mass of the gas flow from the membrane oxygenator to be at least a desired value such that adequate transfer of oxygen and carbon dioxide occurs between the patient's blood and the gas flowing through the membrane oxygenator.

28. A method of delivering a gas to a membrane oxygenator as defined in claim 27 wherein the step of adjusting the pressure of the gas flowing into the inlet of the membrane oxygenator comprises the steps of:

applying a vacuum to the outlet of the membrane oxygenator; and adjusting the pressure at the inlet of the membrane oxygenator to be less than the ambient atmospheric pressure.

29. A method of delivering a gas to a membrane oxygenator as defined in claim 28 wherein the step of regulating the mass of the gas flow from the membrane oxygenator comprises the steps of:

regulating the mass of the gas flow from the gas source to be greater than the mass of the gas flow from the membrane oxygenator.

* * * * *

UNITED STATES PATENT AND TRADEMARK OFFICE
CERTIFICATE OF CORRECTION

PATENT NO. : 5,158,534

DATED : October 27, 1992

INVENTOR(S) : GAYLORD L. BERRY et al.

It is certified that error appears in the above-identified patent and that said Letters Patent is hereby corrected as shown below:

```
Column 1, line 30, "aliments" should be --ailments--
Column 2, line 64, after "advantages" insert --.--
Column 3, line 51, "to oxygen" should be --of oxygen--
Column 4, line 15, "of presently" should be --of the presently--
Column 5, line 52, after "12" insert --.--
Column 7, line 13, "build up" should be --build-up--
Column 9, line 11, delete "of"
Column 10, line 9, "a flow at" should be --flow at a--
Column 11, line 22, in "Part No." column, insert --2k--
Column 47, line 6, delete "a"
Column 47, line 12, delete "a"
```

Signed and Sealed this

Nineteenth Day of October, 1993

*Attest:*

BRUCE LEHMAN

*Attesting Officer*     *Commissioner of Patents and Trademarks*